United States Patent
Morrison et al.

(10) Patent No.: US 10,118,898 B2
(45) Date of Patent: *Nov. 6, 2018

(54) METHOD FOR DECARBOXYLATION OF AMINO ACIDS VIA IMINE FORMATION

(71) Applicant: University of Georgia Research Foundation, Inc., Athens, GA (US)

(72) Inventors: Richard W. Morrison, Watkinsville, GA (US); Douglas Michael Jackson, Athens, GA (US); Daniel Richard Morrison, Watkinsvile, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/249,719

(22) Filed: Aug. 29, 2016

(65) Prior Publication Data

US 2016/0362380 A1    Dec. 15, 2016

Related U.S. Application Data

(63) Continuation-in-part of application No. 14/210,655, filed on Mar. 14, 2014, now Pat. No. 9,452,954.

(60) Provisional application No. 61/783,052, filed on Mar. 14, 2013.

(51) Int. Cl.
| | |
|---|---|
| *C07D 209/14* | (2006.01) |
| *C07D 209/16* | (2006.01) |
| *C07D 233/64* | (2006.01) |
| *C07C 249/02* | (2006.01) |
| *C07C 209/52* | (2006.01) |
| *C07D 207/06* | (2006.01) |
| *C07B 37/06* | (2006.01) |
| *C07C 209/68* | (2006.01) |
| *C07C 213/08* | (2006.01) |
| *C07C 213/02* | (2006.01) |

(52) U.S. Cl.
CPC ........... *C07D 233/64* (2013.01); *C07B 37/06* (2013.01); *C07C 209/52* (2013.01); *C07C 209/68* (2013.01); *C07C 213/02* (2013.01); *C07C 213/08* (2013.01); *C07C 249/02* (2013.01); *C07D 207/06* (2013.01); *C07D 209/16* (2013.01); *C07C 2101/16* (2013.01)

(58) Field of Classification Search
CPC ... C07D 209/14; C07D 209/16; C07D 233/64
See application file for complete search history.

(56) References Cited

U.S. PATENT DOCUMENTS

| | | |
|---|---|---|
| 6,403,806 B1 | 6/2002 | Yeh et al. |
| 7,485,756 B2 | 2/2009 | Omeis et al. |
| 2008/0214864 A1 | 9/2008 | Omeis et al. |

FOREIGN PATENT DOCUMENTS

| | | |
|---|---|---|
| EP | 1586553 | 10/2005 |
| EP | 1586553 B1 | 4/2009 |

OTHER PUBLICATIONS

Galat, A.; Friedman, H.L.. A New Method for the Isolation of Histamine. J. Am. Chem. Soc. 1949. 71, 3976.
Hashimoto, M.; Eda, Y.; Osani, Y.; Iwai, T.; Aoki, S.. A Novel Decarboxylation of α-Amino Acids. A Facile Method of Decarboxylation by the Use of 2-Cyclohexen-1-One as a Catalyst. Chem. Lett. 1986, 6, 893.
Martins, C.P.B., et al. Fingerprint analysis of thermolytic decarboxylation of tryptophan to tryptamine catalyzed by natural oilsJ. Chromatogr. A. 2008, 1210, 115.

*Primary Examiner* — Rebecca L Anderson
(74) *Attorney, Agent, or Firm* — Thomas | Horstemeyer, LLP

(57) ABSTRACT

The present application provides methods for decarboxylation of amino acids via imine formation with a catalyst under pressurized, heated, conditions in either a microwave or oil bath, with optional recovery of the catalyst and/or catalyst byproduct.

23 Claims, 28 Drawing Sheets

Scheme 1

Scheme 2

Microwave Procedure

Oil Bath Procedure

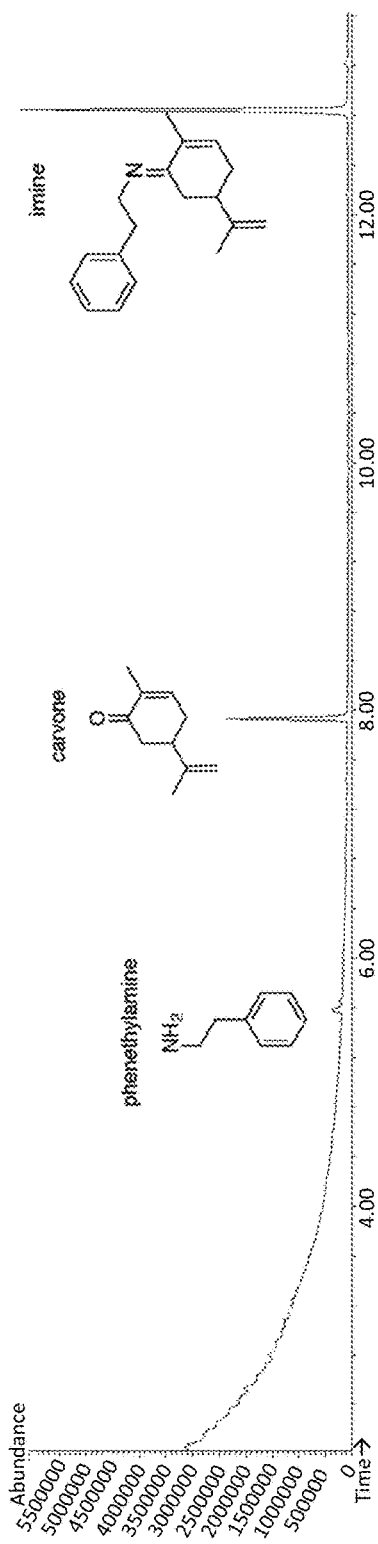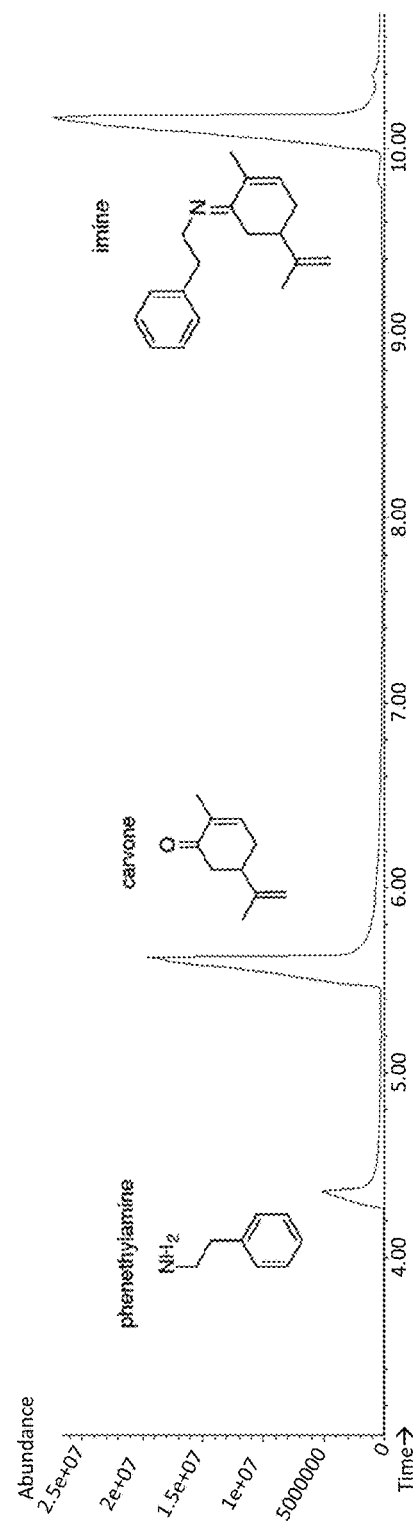
FIG. 8A
FIG. 8B

Dihydrocarvone → Carvenone (H⁺, Heat)

Other examples:

3-ethyl-6-methylcyclohex-2-en-1-one 3-ethylcyclopent-2-en-1-one

Piperitone

Hex-3-en-2-one 2-pentenal

METHOD FOR DECARBOXYLATION OF AMINO ACIDS VIA IMINE FORMATION

CROSS-REFERENCE TO RELATED APPLICATION

This application is a Continuation-in-part of U.S. patent application entitled "Method for Decarboxylation of Amino Acids Via Imine Formation", Ser. No. 14/210,655 filed Mar. 14, 2014 and issued as U.S. Pat. No. 9,452,945 on Sep. 27, 2016, which claims priority to and the benefit of U.S. provisional patent application entitled "Method for Decarboxylation of Amino Acids Via Imine Formation", Ser. No. 61/783,052 filed Mar. 14, 2013, both of which are incorporated herein by reference in their entirety.

BACKGROUND

Decarboxylation of amino acids is an important synthetic route to biologically active amines and other useful byproducts. Current procedures for synthesis of biologically relevant amines suffer from extremely long reaction times and difficulty with solvent and byproduct removal. Thus, an alternative method of isolation for the free amines that is faster than previously reported methods and allows for high yields, solvent removal, and useful byproduct recovery is needed to prevent thermal degradation, particularly for high boiling point product amines.

SUMMARY

Briefly described, the present disclosure provides methods of decarboxylation of amino acids via imine formation at elevated temperatures.

In embodiments, the methods of decarboxylation of amino acids according to the present disclosure include combining, in a pressurized reaction vessel, a mixture of an amino acid, a solvent, and a catalyst, where the catalyst is a ketone, enone, or aldehyde catalyst, or mixture thereof. Then, the mixture is heated at about 180° C., or more, for about 5 minutes, or more, such that the amino acid is converted to its imine. Then the method further includes cooling the reaction vessel to a temperature below the boiling point of the solvent, adding an acid to the cooled reaction mixture in the vessel, and re-heating the acid reaction mixture to a temperature of about 50° C., or more, to hydrolyze the imine to form an amine. The methods of the present disclosure, in embodiments, can be carried out with microwave heating or heating in an oil bath.

In embodiments, the catalyst is selected from the group of ketones, enones and enals consisting of: R-carvone, S-carvone, cyclohex-2-ene-1-one, acetophenone, 3-penten-2-one, butanone, dihydrocarvone, citral, β-ionone, R-pulegone, carvenone, cinnamaldehyde, 3-methylcyclohex-2-enone, pentadione, acetone, piperitone, piperitenone, isopiperitenone, methyl vinyl ketone, butenones, 2-phenylpropenal, and other β-ene-aldehydes. In embodiments, in the imine formation step, the mixture is heated in a microwave to a temperature of about 180° C. to about 190° C. and maintained at a temperature of about 180° C. to about 190° C. for about 5 min to about 10 min. In embodiments, if the reaction mixture is not clear after the first heating step, the mixture is heated to about 180° C. to about 190° C. for about 5 to 20 minutes longer.

In embodiments the catalyst is S-carvone, R-carvone, or dihydrocarvone, or other catalyst capable of isomerization to a useful byproduct, and the acid reaction mixture is heated to about 180° C., or more, to hydrolyze the imine to form an amine and to isomerize any unreacted catalyst to form carvacrol, carvenone, phenolic terpenes (such as thymol) phenolic terpenoids, phenolic structures such as xylenols and ethylmethylphenols, or acyclic and cyclic enals and enones such as, but not limited to, 2-pentenal, hex-3-en-2-one, piperitone and 3-ethylcyclopent-2-ene-1-one. In embodiments the catalyst or isomerized catalyst (e.g., carvacrol, carvenone, etc.) is recovered from the reaction mixture. In embodiments, any unreacted solvent, catalyst, or isomerized catalyst is removed from the reaction mixture and the amine is recovered.

In embodiments, methods of the disclosure include decarboxylation of amino acids via imine formation, where the method includes combining, in a pressurized reaction vessel, a mixture of an amino acid, a solvent, and a catalyst, where the catalyst is a ketone or enone; heating the mixture at about 180° C., or more, for about 5 minutes, or more, such that the amino acid is converted to its imine; and recovering the imine.

Other systems, methods, features, and advantages of the present disclosure will be or become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

Many aspects of the disclosed methods can be better understood with reference to the drawings, which are discussed in the description and examples below. The components in the drawings are not necessarily to scale, emphasis instead being placed upon clearly illustrating the relevant principles of the present disclosure.

FIG. 8A illustrates a GC post-decarboxylation with imine predominant at >95%, as compared to free amine. FIG. 8B is a GC illustrating product mixture after low temperature partial hydrolysis in aqueous acid. Increased amounts of free amine and carvone are present relative to imine.

DESCRIPTION

Figure 1:
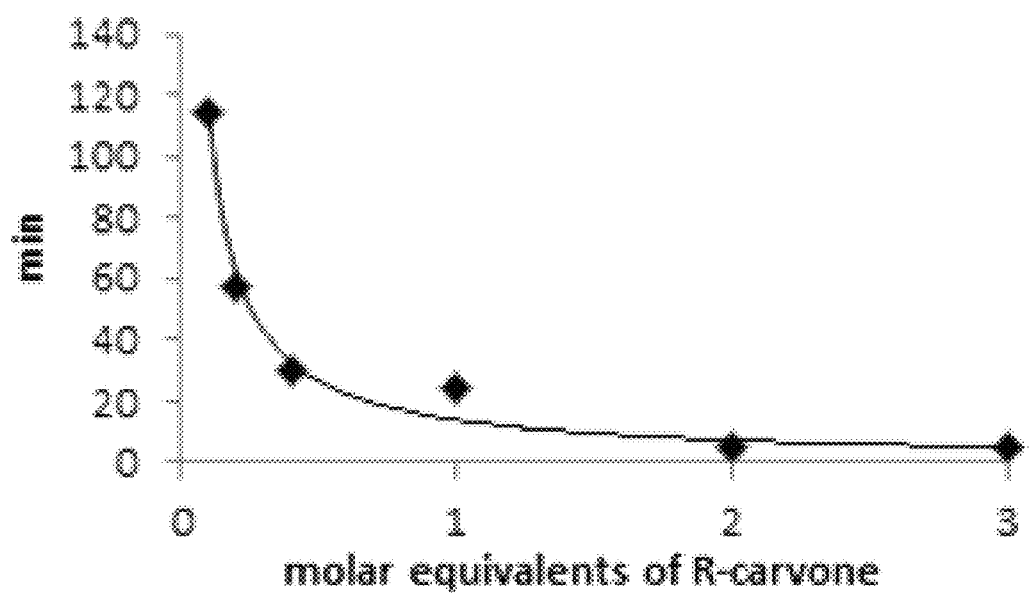
FIG. 1 is a graph illustrating the reaction time in minutes for a series of microwave assisted decarboxylations of phenylalanine in n-propanol at 190° C. with various levels of R-carvone as catalyst.

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. Terms defined in references that are incorporated by reference do not alter definitions of terms defined in the present disclosure or should such terms be used to define terms in the present disclosure they should only be used in a manner that is inconsistent with the present disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, organic and inorganic chemistry, material science, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DISCUSSION

Embodiments of the present disclosure provide for methods of decarboxylation of amino acids (including both naturally occurring amino acids and synthetic analogs) to amines with the concurrent production of useful byproducts. The methods of the present disclosure provide for a quick, simple and effective decarboxylation of amino acids via imine formation with a catalyst under heated, pressurized conditions with consequent recovery of product amines and catalyst byproducts.

Enzymatic decarboxylation of amino acids occurs in many organisms and provides a synthetic option for the decarboxylation of amino acids, such as L-histidine. Many amino acids have also been shown to undergo decarboxylation upon reflux in a high boiling solvent, such as cyclohexanol, in the presence of a ketone, such as cyclohex-2-ene-I-one or acetophenone. This is believed to occur through an active conformation of an imine intermediate. However, for synthesis of some of the more biologically relevant amines, previously reported procedures are slow and are complicated by difficult purification procedures to remove byproducts and high boiling solvents.

More recently, two processes for the removal of product free amines by distillation from a high boiling solvent have been reported. These methods may assist with the problem of solvent removal for lower boiling product amines, but reaction times were still extremely long and the success of these procedures for difficult decarboxylations, such as L-histidine to histamine, are unsubstantiated and have not been reproduced. Thus, an alternative method of isolation is needed to prevent thermal degradation, especially for free amines with a high boiling point.

Embodiments of the methods for decarboxylation of amino acids of the present disclosure include combining an amino acid, a solvent, and a catalyst in a pressurized reaction vessel to form a mixture. The mixture is then heated at a temperature of at least about 180° C. (e.g., about 180° C., or more) for at least 5 minutes, or more. During heating, the reaction takes place to convert the amino acid to its imine. The resulting reaction mixture in the vessel includes the imine, the solvent, any unreacted catalyst, and any unreacted amino acid. If the reaction is not complete (in embodiments, a complete reaction is indicated by the reaction mixture turning from a slurry into a clear liquid), additional heating is performed, as described below.

Various solvents can be used in the methods of the present disclosure, but an advantage of the present methods is that a solvent with greater volatility and lower boiling point provides advantages over the traditional cyclohexanol used in previous, time consuming methods. Thus, various solvents with a lower boiling point than traditional solvents for conversion of amino acids to amines can be used. In embodiments, the solvent does not produce a maximum vapor pressure exceeding the vessel limit. Thus, the solvent system can be tailored to the parameters of the reaction vessel and vice versa. In embodiments, the reaction vessel is a 15 bar reaction vessel. In embodiments the solvent is a short chain alcohol or water. Solvents that can be used in the methods of the present disclosure include, but are not limited to, water, n-butanol, n-pentanol, isopropanol, ethanol, methanol, n-propanol, and combinations of these solvents. In embodiments of the methods of the present disclosure, the solvent is n-propanol.

Various catalysts can also be used in the methods of the present disclosure. Some examples of catalysts that can be used in the methods of the present disclosure include, but are not limited to, ketone, enone, enal, and/or aldehyde catalysts including, but not limited to, cyclohex-2-ene-1-one, acetophenone, 3-penten-2-one, butanone, dihydrocarvone, R-carvone, S-carvone, β-ionone, R-pulegone, 3-methylcyclohex-2-enone, carvenone, citral, piperitone, piperitenone, isopiperitenone, methyl vinyl ketone, butenones, acetone, cinnamaldehyde, pentadione, 2-phenylpropenal (CAS 4432-63-7), and other β-ene-aldehydes. In embodiments, the catalyst is an enone or enal capable of isomerization (e.g., at temperatures of about 180° C., or more) to yield a phenolic terpene or phenolic terpenoid byproduct. In embodiments, the catalyst is an alpha, beta-unsaturated ketone. In embodiments, the catalyst is an enone. In embodiments enone catalysts can include enones such as, but not limited to, R-carvone, S-carvone, citral, 3-penten-2-one, cyclohex-2-ene-1-one, β-ionone, R-pulegone, carvenone, piperitenone, isopiperitenone, and 3-methylcyclohex-2-enone. In embodiments of the present disclosure, the catalyst is R- or S-carvone. In embodiments, the catalyst is an enal such as cinnamaldehyde or 2-ene-propanal.

The catalyst used in the methods of the present disclosure can also lead to useful byproducts that can later be recovered and isolated for other purposes. In some embodiments, the catalyst isomerizes during decarboxylation reaction at higher temperatures to produce a useful byproduct. Some such isomerized catalyst byproducts have commercial importance, and the methods of the present disclosure provide efficient production of such byproducts.

For instance, carvone isomerizes to carvacrol due to keto-enol tautomerism and acid-catalyzed alkene migration, driven by the stability of the resulting aromatic system. Carvacrol is a monoterpenoid phenol with odor of oregano and is used for many commercial purposes. Similarly, the ketone catalyst dihydrocarvone also isomerizes undergoing acid catalyzed alkene migration similar to carvone resulting in the alpha, beta-unsaturated enone carvenone. Carvenone is thus also a useful catalyst byproduct that can, itself, be used as a catalyst for the decarboxylation process of the present disclosure.

Other enone catalysts, such as piperitenone and isopiperitenone, can isomerize to produce thymols. Other phenolic terpenes and terpenoids, other phenolic structures (such as, but not limited to xylenols and ethylmethylphenols), and other acyclic and cyclic enal and enone analogs of carvenone (such as, but not limited to 2-pentenal, hex-3-en-2-one, piperitone and 3-ethylcyclopent-2-ene-1-one) can be produced in good yields in the methods of the present disclosure as byproducts from suitable enone and or ketone precursors/catalysts. The structural features and reaction conditions appropriate for isomerization are discussed in greater detail in the Examples below.

In some embodiments, enone and/or enal catalysts, cyclohexanone, acetophenone and other aryl-substituted aldehydes, may not undergo isomerization and remain in their original forms during the reaction and would be removed at the end of the reaction for later re-use.

In an embodiment, use of the enones R- or S-carvone in methods of the present disclosure for decarboxylation of amino acids leads to the formation of carvacrol as a byproduct. Carvacrol, a component of oil of oregano, is a useful volatile compound that can be recovered and used in the flavoring industry as well as other uses. In other embodiments, use of the ketone dihydrocarvone as catalyst leads to the formation of carvenone as byproduct. Carvenone can also be used as a catalyst in the methods of the present disclosure. In embodiments, such byproducts can be recovered as described below. In embodiments, the catalysts piperitenone or isopiperitenone can be used as catalysts for the decarboxylation and can isomerize to produce thymol.

As described in the examples below, the load of the catalyst is a factor affecting the reaction rate and ease of purification. It was found that 0.1 mole equivalents of catalyst produced an appreciable catalytic effect and that the effect appeared to peak at about 2 mole equivalents. Thus, in embodiments, the mixture includes from about 0.1 to about 2 mole equivalents of catalyst.

In the methods of the present disclosure, the heating can be performed in a microwave or, alternatively, in traditional oil bath. In some embodiments using the oil bath for heating, the oil can be, but is not limited to, silicone oil. In embodiments, the initial mixture of amino acid, solvent, and catalyst is heated in a microwave to a temperature of about 180° C. to about 190° C. for about 5 min to about 10 min. In embodiments, a microwave reactor with a thermometer and automatic feedback loop is used to maintain the temperature. After the initial heating, if the reaction mixture is not complete (e.g., not clear, or other criteria, as applicable) a second heating step can be conducted. In embodiments, the mixture is re-heated in the microwave to about 190° C. for about 5 to about 25 min longer.

When an oil bath is used, additional heating time may be needed, since it is more difficult to maintain a constant heat in the oil bath. In embodiments, the initial mixture of amino acid, solvent, and catalyst is heated in an oil bath at a temperature of about 180° C. to about 190° C. for about 5 min to about 20 min. In embodiments, if the reaction is not complete after the first heating, an additional heating can be conducted, such as by heating again at about 180° C. to about 190° C. for about 5 to about 20 min longer. To account for changes in temperature of the oil bath when the room temperature reaction vessel is added, the oil bath may be heated to a higher temperature prior to addition of the reaction vessel. For instance, in embodiments, the oil bath is heated to a temperature of about 210° C. prior to addition of the reaction vessel and brought back to a temperature between about 185° C. to about 190° C. after addition of the reaction vessel. This effect is mitigated by increasingly large bath volume.

After the heating steps, the amino acid will be substantially converted to its imine. To achieve high yield of amine from the imine, a hydrolysis step can be added. Hydrolysis can be achieved by heating in acid. Acids, such as, but not limited to HCl, can be used in the methods of the present disclosure. In embodiments, the methods include cooling the reaction vessel to a temperature below the boiling point of the solvent, adding an acid to the reaction mixture in the vessel, and heating the acid reaction mixture to about 50° C., or more, to hydrolyze the imine to form an amine.

In embodiments, the catalyst can be recovered from the reaction mixture by conducting the acid heating step at a temperature of about 50-100° C. (for instance, 80° C.), with gentle reflux to hydrolyze the imine in equilibrium. When the catalyst is carvone or dihydrocarvone, and the gentle reflux is conducted between about 50-100° C., for instance at about 80° C., the catalyst is not isomerized and can be recovered via extraction with diethyl ether or other appropriate extraction method.

In some embodiments, the catalyst can be isomerized to a useful byproduct. Isomerization can be done after extracting the catalyst, or it can be done during or after the acid hydrolysis step without first extracting the catalyst. For instance, in embodiments, remaining unreacted carvone can be isomerized to carvacrol by heating at a temperature of about 120° C., or more (e.g., about 150° C. or more, about 180° C., or more, etc.), for about 5 min, or more. While some other ketone, enone, and aldehyde catalysts in addition to carvone, for example dihydrocarvone, isomerize in acidic reaction conditions at temperatures above about 120° C. or above about 180° C. (or other intermediate range, e.g., between about 120° C. and about 180° C.), as described above, other catalysts remain in their original form (even after heating to over 180° C. in acid) and must be recovered via isolation/purification methods such as extraction with diethyl ether. Isomerization of R-Carvone and S-Carvone to carvacrol is advantageous due to its ability to drive the hydrolysis equilibrium.

In some embodiments, before, after, or instead of recovering the unreacted catalyst, the unreacted catalyst (e.g., carvone or dihydrocarvone) is isomerized to a useful catalyst byproduct (e.g., carvacrol or carvenone, respectively) by heating the mixture (during or after acid hydrolysis) at a temperature of about 120° C. or above, for instance at about 120° C. to about 190° C., for about 5 min, or more. In embodiments, the catalyst isomerization is done by heating the mixture at a temperature of about 180° C., or more, for about 5 min, or more. In embodiments, the catalyst byproduct, such as carvacrol or carvenone, is extracted from the amine product by methods such as ether extraction. Extraction may be accomplished using various organic solvents including, but not limited to, diethyl ether. For instance, carvacrol and/or carvenone can be recovered by extraction with diethyl ether. In some instances, carvacrol may be carefully decanted from the reaction vessel as it sometimes forms a distinct liquid layer at the top of the reaction vessel prior to the addition of an organic extraction solvent. Catalysts and catalyst byproducts (e.g., carvacrol, carvenone, piperitone, etc.) may also be isolated and/or further purified via other means, such as distillation, known to those of skill in the art.

In some embodiments, greater purity of amine product is possible if the acid heating step is conducted at higher temperatures, such as above about 180° C., to isomerize the catalyst, as described above, during the hydrolysis of the imine with acid. Thus, in embodiments, the acid reaction mixture is heated to about 180° C., or more, for about 5 min., or more, to hydrolyze the imine to form an amine and to isomerize any unreacted catalyst. In embodiments, the acid reaction mixture is heated at about 185° C. to about 190° C. for about 5 min, or more. In embodiments, the acid is HCl. In embodiments the acid is 2M HCl. In some embodiments, such as when the products and/or amino acids are sensitive to acid during hydrolysis at 180° C., hydrolysis at 80° C. with soxhlet extraction, for removal of catalyst, can be performed instead.

After hydrolysis of the imine in acid, the unreacted catalyst or catalyst byproduct and solvent can be removed by washing with water and organic solvent (e.g. an ethyl solvent, such as, but not limited to, diethyl ether). The corresponding amine acid or amine salt (e.g. amine hydrochloride or dihydrochloride salt) can be recovered by distilling off the solvent and water. The washing and distillation step can be repeated as necessary. In embodiments the reaction mixture is washed three times with ether and water solvent. In embodiments, after washing and distilling off the water and solvent, the amine salt can be dried (e.g., in an oven).

The above methods of the present disclosure can be conducted with any amino acids where it is desirable to convert the amino acid to the corresponding amine. Some exemplary amino acids that can be used in the methods of the present disclosure include, but are not limited to, histidine, isoleucine, lysine, phenylalanine, tryptophan, tyrosine, glycine, alanine, valine, proline, leucine, and threonine. Amino acids suitable for decarboxylation according to the methods of the present disclosure also include synthetic amino acids and other non-naturally occurring amino acid analogs. In accordance with standard nomenclature, amino acid residues are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). As used herein the term "amino acid" refers to either natural and/or unnatural or synthetic amino acids, including glycine and both the D or L optical isomers, cyclopropyl-, cyclobutyl-, cyclopentyl- and cyclohexyl-containing synthetic amino acids, and amino acid analogs and peptidomimetics.

As described in the examples below, in embodiments of the present disclosure methods of rapid decarboxylation of L-histidine and other L-amino acids have been accomplished via stable imine formation with R-carvone, and other catalysts, with subsequent one-pot hydrolysis under solvent superheated conditions using both conventional heating and microwave radiation. Although described in greater detail in the example below, briefly described, in an embodiment, the amino acid and R-carvone in a solvent of n-propanol are sealed in a suitable 15 bar microwave vessel with magnetic stirring. Decarboxylation is rapid (5-20 min) as the vessels are heated to about 190° C. over 5 min. The formed R-carvone imines are stable at room temperature in aqueous acid. An additional 5 min period of heating may be performed if reaction is not complete.

Next, hydrolysis can be achieved by heating in acid (e.g., HCl) in one-pot fashion. In an embodiment, the reaction vessel is cooled to a temperature below the boiling point of the solvent, acid is added to the reaction mixture in the vessel, and the acid reaction mixture is heated to about 50° C. to about 185° C., to hydrolyze the imine to form an amine and optionally (at temps of about 180° C. or higher) isomerize R-carvone to carvacrol and drive the reaction to completion. In some embodiments, approximately 80% of the R-carvone can be recovered via extraction with diethyl ether if the hydrolysis is conducted at about 80° C.

In some embodiments, greater amounts of catalyst can be recovered if the 80° C. hydrolysis is conducted in a soxhlet extractor with an organic solvent of boiling point 80° C. or greater such as, but not limited to, toluene. In some embodiments, the products and/or amino acids proved sensitive to acid during hydrolysis at 180° C. In these cases, the 80° C. hydrolysis with soxhlet extraction provided a solution. In other embodiments, to obtain high product purity, residual catalyst (e.g., S- or R-carvone or dihydrocarvone) is isomerized to a byproduct, such as carvacrol or carvenone, for easy removal as described above and demonstrated in the examples below. In embodiments, the catalyst byproduct is then extracted away with diethyl ether, and water is removed via evaporation under reduced pressure. In embodiments, the catalyst byproduct is also recovered as a useful product, such as carvacrol, useful as essential oils, and dihydrocarvone, which may also be a useful catalyst for the present amino acid decarboxylation. The entire conversion from amino acid to amine hydrochloride or dihydrochloride salt, as appropriate, was accomplished in less than 2 hours in all cases, followed by oven drying with isolated yields of 60-90%.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere. In the pressurized reaction vessels of the present disclosure, pressure is greater than 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

Now having described the embodiments of the disclosure, in general, the following examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

EXAMPLES

The following examples describe decarboxylation of L-histidine and other L-amino acids via imine formation with R-carvone and other catalysts with subsequent one-pot hydrolysis under solvent superheated conditions using both conventional heating and microwave radiation.

Example 1—Decarboxylation of Amino Acids Via Imine Intermediate

This example describes decarboxylation of various amino acids using the methods described above with R-carvone and other catalysts. Decarboxylation was more rapid (5-20 min) than previous methods as the vessels were heated to 190° C. over 5 min. Approximately 80% of the R-carvone could be recovered via extraction with diethyl ether when the hydrolysis was conducted at 80° C. To obtain a higher purity product, a high temperature hydrolysis was conducted to isomerize residual R-carvone to carvacrol. Isolated yields of amine hydrochloride salts were comparable or improved over previous methods ranging from 60-90%. Given the exceptionally clean 1H NMR spectra and simplicity of the procedure, purity of hydrochloride salts was estimated to be >99% by 1H NMR.

Materials and Methods 5 mmol scale microwave experiments were performed in Milestone 25 mL 15 bar glass pressure reactors inside the Milestone Start SYNTH microwave oven with external infrared temperature control. Traditional heating experiments were performed in silicone oil in the same reaction vessels. Solvents and reagents were purchased from Sigma-Aldrich and used without additional purification. FT NMR experiments were recorded at 400 MHz in a solvent of $D_2O$.

General "One-Pot" Procedure for the Decarboxylation of Amino Acids

A magnetic stir bar, 3 mL of n-PrOH, 10 mmol of R-Carvone, and 5 mmol of amino acid were charged to a pressure vessel. The vessel was heated from room temperature to 190° C. over 5 min with stirring. If necessary the reaction vessel was maintained at 190° C. for additional time until the slurry became clear. The vessel was allowed to cool to below the solvent boiling point, carefully vented to release evolved $CO_2$, and 10 mL of 2M HCl was added. The vessel was heated to 190° C. over 5 min with stirring and allowed to cool. The aqueous reaction mixture was washed three times with 25 mL of ether and water solvent distilled off from the hydrochloride salt. The hydrochloride salt was transferred to a vacuum oven and dried overnight at 150° C. and 10 Torr. The hydrochloride salt was then weighed and analyzed via IR and NMR.

methylamine hydrochloride, $\delta_H$ 2.44 s; $\delta_C$ 24.5 ethylamine hydrochloride, $\delta_H$ 1.10 3H t J=8, 2.88 2H q J=8; $\delta_C$ 11.7, 35.1

2-methylpropan-1-amine hydrochloride, $\delta_H$ 0.83 6H d J=4, 1.79 1H m J=8, 2.69 2H d J=8; $\delta_C$ 18.8, 26.2, 46.3 pyrrolidine hydrochloride, $\delta_H$ 1.83 4H t J=4, 3.11 4H t J=4; $\delta_C$ 23.6, 45.4

3-methylbutan-1-amine hydrochloride, $\delta_H$ 0.75 6 H d J=4, 1.38 2H q J=8, 1.48 1H m J=8, 2.85 2H t J=8; $\delta_C$ 21.28, 24.87, 35.43, 37.87

1-aminopropan-2-ol hydrochloride, $\delta_H$ 1.08 3H d J=4, 2.73 1H dd J=8, 2.95 1H dd J=12, 3.88 1H m J=4; $\delta_C$ 19.54, 45.46, 63.83 histamine dihydrochloride, $\delta_H$ 3.00 2 H t J=8, 3.18 2H t J=8, 7.23 1H s, 8.50 1H s; $\delta_C$ 22.26, 38.11, 117.08, 128.49, 134.00 tryptamine hydrochloride, $\delta_H$ 2.97 2H t J=9, 3.13 2H t J=8, 7.01 1H t J=4, 7.07-7.12 2H m, 7.34 1H d J=4, 7.49 1H d J=4; $\delta_C$ 22.88, 40.03, 109.36, 112.30, 118.54, 119.68, 122.44, 124.53, 126.70, 136.69

2-methyl-1-butylamine hydrochloride $\delta_H$ 0.71 3Ht J=8, 0.78 3Hd J=8, 1.02 1H septet J=8, 1.22 1H septet J=8, 1.55 1 Ho J=8, 2.59-2.64 1 Hm, 2.76-2.80 1H m; $\delta_C$ 10.07, 15.75, 25.94, 32.48, 44.75 cadaverine dihydrochloride $\delta_H$ 1.28 2H p J=8, 1.54 4H p J=8, 2.84 4H t J=8; $\delta_C$ 22.75, 26.32, 39.33 tyramine hydrochloride $\delta_H$ 2.75 2H t J=8, 3.06 2H t J=8, 6.73 2H d J=8, 7.04 2H d J=8; $\delta_C$ 31.95, 40.83, 115.90, 128.55, 130.32, 154.65

2-phenylethylamine hydrochloride $\delta_H$ 2.82 2H t J=8, 3.10 2H t J=8, 7.12-7.26 5H m; $\delta_C$ 32.73, 40.55, 127.30, 128.88, 163.03, 170.53

Results and Discussion

Addressing the problem of long reaction times required for the decarboxylation of many amino acids such as histidine (>40 hrs) using extant procedures, it was envisioned that chemistry at temperatures above the reflux temperature of cyclohexanol (~160° C.) may provide a solution. However, in earlier efforts a significant amount of effort had been devoted to the removal of cyclohexanol and other high boiling solvents at the expense of yield and efficiency. An advantage to using a nonpolar alcohol, such as cyclohexanol, as solvent was the solubility of the amine product and insolubility of amino acids, thus allowing for visual determination of reaction completion (from slurry to clear solution). Rather than employ a higher boiling solvent system, which would yield the same difficulties as seen in the conventional methods, the possibility of a pressurized reaction system using a solvent with a lower normal boiling point was investigated in the present example.

Both microwave-promoted and hot oil bath systems were investigated, using a sealed 15 bar maximum pressure reaction vessel. While many solvents satisfy the criterion of greater volatility, the search was limited to a series of short chain alcohol solvents in order to promote microwave absorption.

Decarboxylation in aprotic solvents (microwave transparent) was observed to be slower when performed in an oil bath. Among the short chain alcohol solvents and water, n-butanol, n-pentanol, and isopropanol proved to absorb microwaves insufficiently, while ethanol, methanol, and water dissolve the reactant amino acid at the optimum reaction temperatures of >185° C., potentially hindering determination of reaction completion. Ethanol and methanol also require vessels that can withstand higher vapor pressure to achieve the optimum reaction temperature. An optimum solvent for visual inspection of reaction completion that could also reach the desired temperature without exceeding the maximum vapor pressure and could be removed easily after reaction completion was found to be n-propanol. This solvent achieves a maximum temperature of 190° C. (calibrated +/−2° C.) in a 1200 W instrument with a vapor pressure of 15 bar according to the Clausius-Ciaperyon equation. It should be noted that other (even nonpolar) solvents should also prove effective when heating in an oil bath so long as the maximum vapor pressure does not exceed the vessel's rated limit. However, reactions performed neat resulted in poor yield and aprotic solvents failed to promote decarboxylation even in the oil bath.

Figure 3:
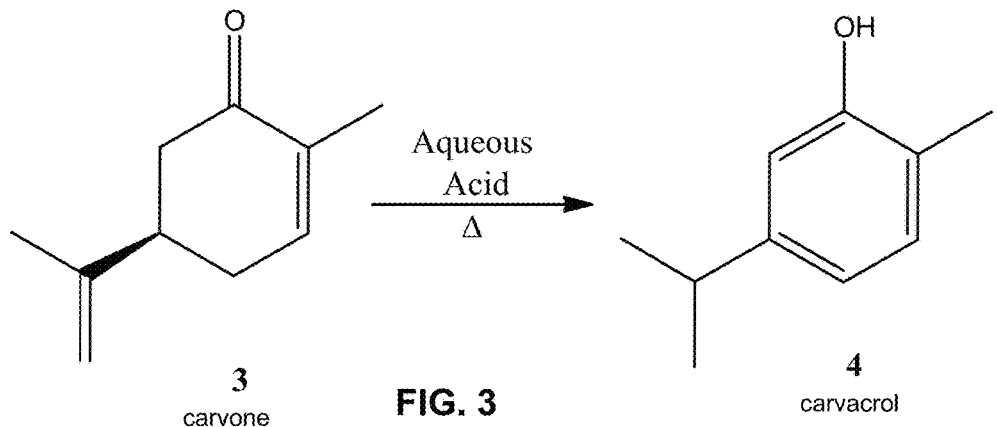
FIG. 3 illustrates the isomerization of carvone to carvacrol in aqueous acid, which facilitates its removal from the reaction product by basic extraction.

Another factor affecting the reaction rate and overall ease of purification of the product mixture was the identity and load of the catalyst. In conventional methods, a 1% v/v of cyclohex-2-ene-1-one (2) has been reported for histidine decarboxylation; however, others have reported difficulty in repeating these results without a substantially higher catalyst load. Significant impurities were also observed in the resulting reaction mixture by those authors, and in later attempts to reproduce the experiments. These authors alternatively used acetophenone (1) to modest success for the decarboxylation of histamine at 20 mol % in >40 hr. It was postulated that the greater the stability of the imine, the greater the reaction rate at a given catalyst load, and, indeed, cyclohex-2-ene-1-one (2) proved to provide a greater catalytic effect at 20 mol % than acetophenone (1). On a belief that the enone functionality of cyclohex-2-ene-1-one provides some advantage over the benzyl ketone and, given its toxicity and expense, an alternative was selected for testing in the present examples. R-carvone (3), the natural product of spearmint oil, was selected for its potential to retain the catalytic advantage over acetophenone while providing an alternative method of removal of the catalyst based on the isomerization reaction of R-carvone (3) to carvacrol (4) (Scheme 1, FIG. 3).

It was also observed during these experiments that the rate of reaction significantly increased at the higher catalyst load, an effect maximizing at about 2 mole equivalents for both cyclo-hex-2-ene-1-one (2) and R-carvone (3). The reaction times in minutes of a series of microwave assisted decarboxylations of phenylalanine in n-propanol at 190° C., varying the load of R-carvone (3) catalyst, are given in FIG. 1. Table 1, below, compares several catalysts at the 2 equivalent load for performance on a series of decarboxylations.

Figure 2A:
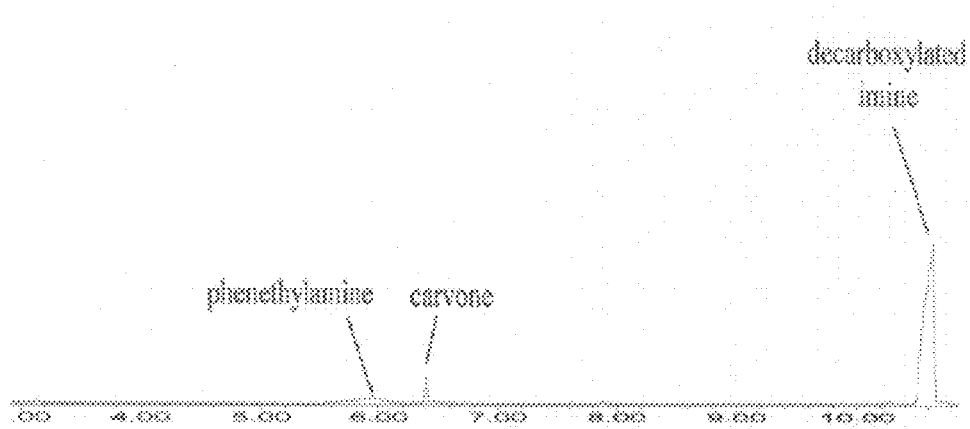
FIG. 2A is a GC-MS spectrum of the reaction product of the decarboxylation of phenylalanine with carvone.
Figure 2B:
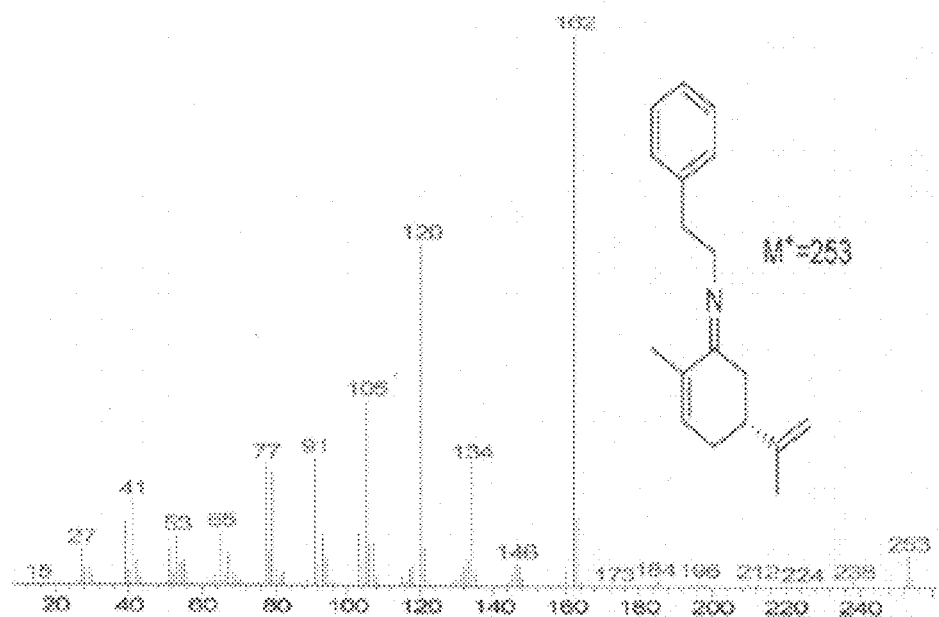
FIG. 2B is a gas chromatograph of the crude product of decarboxylation of phenylalanine in the presence of 2.0 mole equivalents of R-carvone after workup in aqueous acid. The EI mass spectrum of the imine of phenethylamine and carvone is clearly shown as the predominant species.

Considering that the reaction is thought to occur through a carboxylic acid imine intermediate and given the observed rise in impurities as a result of increasing the catalyst load from the Hashimoto procedure, the fate of the decarboxylated imine was then investigated as follows. A large excess of carvone was added to the reaction mixture to attempt to capture all product amine as an imine with carvone. The imine was then transferred into an aqueous acid mixture, excess carvone removed via ether wash, and then returned to an organic phase via neutralization with NaOH solution. A significant degree of hydrolysis was expected; however, in these observations, the imine of the decarboxylated product was quite stable and persisted as demonstrated by the GC-MS spectrum and gas chromatograph (FIGS. 2A and 2B) of the product mixture of decarboxylated phenylalanine.

It was observed that only after heating in acid at >50° C. did the hydrolysis occur. Even after one pot reflux with many times the reaction volume of 2.0 M HCl, it proved difficult to adequately remove all traces of the imine at system equilibrium. Each conventional method of amino acid decarboxylation fails to account for the quantity of imine that may remain, thus lowering the yield and purity of the crude product and leading to further purification.

It was envisioned that the complete hydrolysis of the imine could be accomplished via the removal of the catalyst in situ. If a low boiling ketone, such as acetone, or other aldehyde catalyst were used, it would be sealed in the pressurized vessel during decarboxylation and then distilled away from the product mixture during imine hydrolysis. Several decarboxylations were accomplished using acetone as catalyst; however, the vapor pressure of pure acetone at the optimal temperature exceeded the recommended safe operating pressure of the reaction vessel so an alternative option was desired. Thus, R-carvone (3), an inexpensive, readily available alpha unsaturated ketone natural product, was selected. The isomerization reaction of carvone produces carvacrol (FIG. 3), a phenolic natural product that would be inert to the product amine and is also a useful compound that can be recovered for other uses (e.g., oil of oregano), as described in greater detail in Example 2.

Using R-carvone as catalyst, a 5 min reflux at 190° C. in 2 M HCl hydrolyzed the imine and isomerized carvone to carvacrol. The carvacrol was then easily removed via ether extraction. It should be noted that gentle reflux at 80° C. allows the imine to hydrolyze in equilibrium, and ~80% of the carvone catalyst may be recovered via three sequential refluxes and extractions. If the carvone is recovered in this way, a final high temperature reflux can be performed to isomerize residual carvone to carvacrol for isolation of amine hydrochloride salt of highest purity. The overall synthetic process is highlighted in Scheme 2, illustrated in FIGS. 4A-B.

Figure 4A:
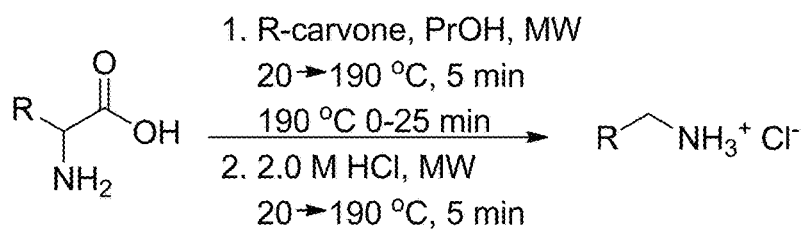
FIGS. 4A-B illustrates a reaction scheme (scheme 1) for a one-pot decarboxylation procedure.
Figure 4B:
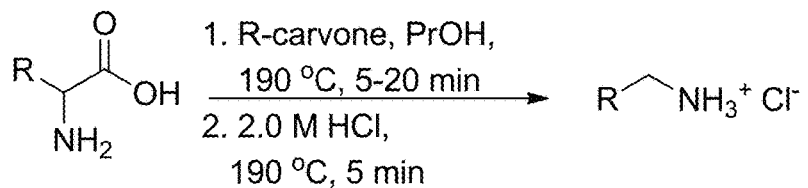

The reaction times for the decarboxylation of selected amino acids of interest is reported in Table 2, below, for both microwave and oil bath heating. Isolated yields of the amine hydrochloride or dihydrochloride salts are also given in Table 2 for the optimized reaction conditions highlighted in reaction Scheme 2 (FIGS. 4A-B). The slight differences in the overall reaction times reported between MW heating and oil bath heating are the result of the differences in the experimental procedure. In the microwave reactor initial heating is rapid, occurring over a 5 min period, and temperature is computer controlled by an infrared thermometer in a continuous feedback system to +/−2° C. Conventional heating was performed in a preheated bath with observed temperature oscillations of about +/−5° C. For example, in some experiments the reaction vessels were added to a pre-heated oil bath system at ~210° C., which, upon addition of the room temperature vessels, dropped to ~185° C., where the temperature was maintained as close to 190° C. as possible (typically to within ±5° C.).

Figure 5:
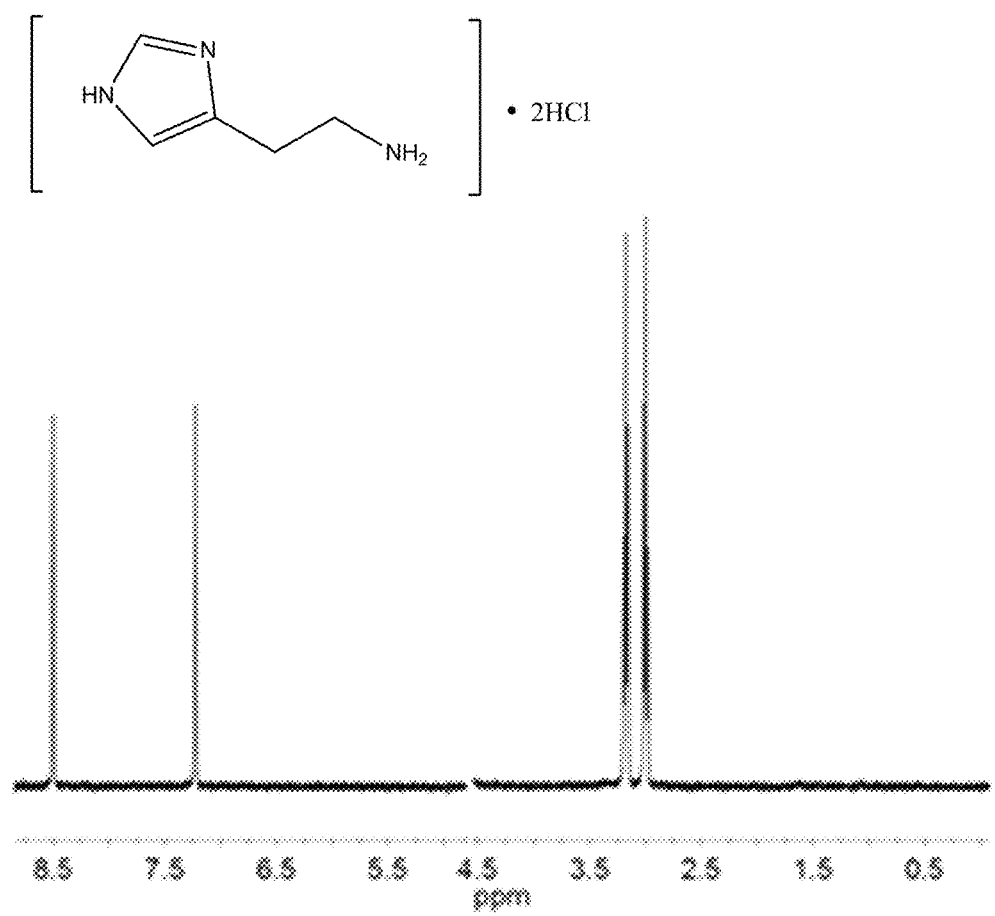
FIG. 5 illustrates an HNMR of histamine dihydrochloride with solvent $D_2O$ suppressed.

A representative HNMR is shown in FIG. 5 for the product amine salts in $D_2O$. The solvent peak arising from acidic proton exchange was suppressed. Note that no organic impurities were observed in H NMR of the hydrochloride salts using DMSO-$d_6$ as solvent.

TABLE 1

Reaction times in minutes at the 2.0 molar equivalent load for various catalysts for a series of decarboxylations under MW conditions at 190° C.

| Amino Acid | Acetophenone (1) | Cyclohex-2-ene-1-one (2) | R-carvone (3) | S-carvone | acetone |
|---|---|---|---|---|---|
| Phe | 5 | 5 | 5 | 7 | 5 |
| His | 25 | 25 | 25 | 50 | * |
| Trp | 5 | 5 | 5 | 5 | 7 |
| Tyr | 10 | 6 | 20 | 16 | 40 |

* completed in approximately 72 hours in an oil bath

TABLE 2

Decarboxylation reaction times and yields for a series of amino acids under optimized conditions heated by either MW irradiation or via oil bath.

| Conditions | Amino Acid | Reaction Time (min) | Yield (%) |
|---|---|---|---|
| MW* | His | 25 | 87 |
| | Ile | 9 | 69 |
| | Lys | 12 | 73 |
| | Phe | 5 | 76 |
| | Trp | 5 | 68 |
| | Tyr | 20 | 53 |
| | Gly | 13 | 86 |
| | Ala | 5 | 60 |
| | Val | 5 | 79 |
| | Pro | 5 | 80 |
| | Leu | 5 | 72 |
| | Thr | 5 | 59** |
| Oil Bath | His | 12 | 92 |
| | Ile | 12 | 76 |
| | Lys | 17 | 93 |
| | Phe | 5 | 78 |
| | Trp | 9 | 72 |
| | Tyr | 40 | 67 |
| | Gly | 40 | 67 |
| | Ala | 38 | 74 |
| | Val | 9 | 55 |
| | Pro | 5 | 48 |
| | Leu | 5 | 69 |
| | Thr | 12 | 41** |

*reaction times represent total programmed time
**80° C. hydrolysis with soxhlet extraction performed

Example 2—Carvone to Carvacrol Conversion and Isolation in Organocatalytic Decarboxylation of Amino Acids This example provides experimental evidence concerning the optional conversion of an enone decarboxylation catalyst, carvone, to useful byproduct carvacrol, the phenolic oil of oregano, and recovery of this formed essential oil. Additionally, this conversion efficiently drives the conversion of imine decarboxylation intermediate species to product free amine described in the examples above.

Such a conversion of the catalyst to a useful byproduct is unique to catalysts with potential for structural rearrangement forming an aromatic phenol ring. The carvone "R" and "S" stereoisomers have an exocyclic unsaturation, which is incorporated into the ring in acidic conditions causing a net conversion of enone to phenol functionality, as illustrated below. Only cyclic enones exist in natural equilibrium with enol tautomers with extended conjugated electron systems that invite isomerization. The exocyclic unsaturation migrates to the ring in acidic conditions to form the highly stable phenolic system. Carvone is a cheaply available natural oil fitting the criteria of cyclic enone with the exocyclic unsaturation.

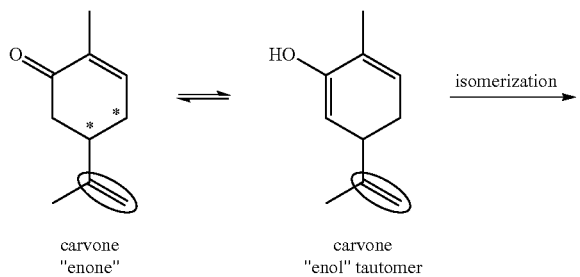

carvone "enone"    carvone "enol" tautomer    isomerization

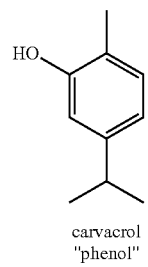

carvacrol "phenol"

*positions where exocyclic unsaturation results in isomerization (exocyclic unsaturation circled)

In general, enone and ketone catalysts, which lack one or both of these criteria, will also catalyze decarboxylation on amino acids as described above, but must be removed in several purification steps and are not isomerized in such a way as the cyclic enones.

Methods and Results

Figure 6A:
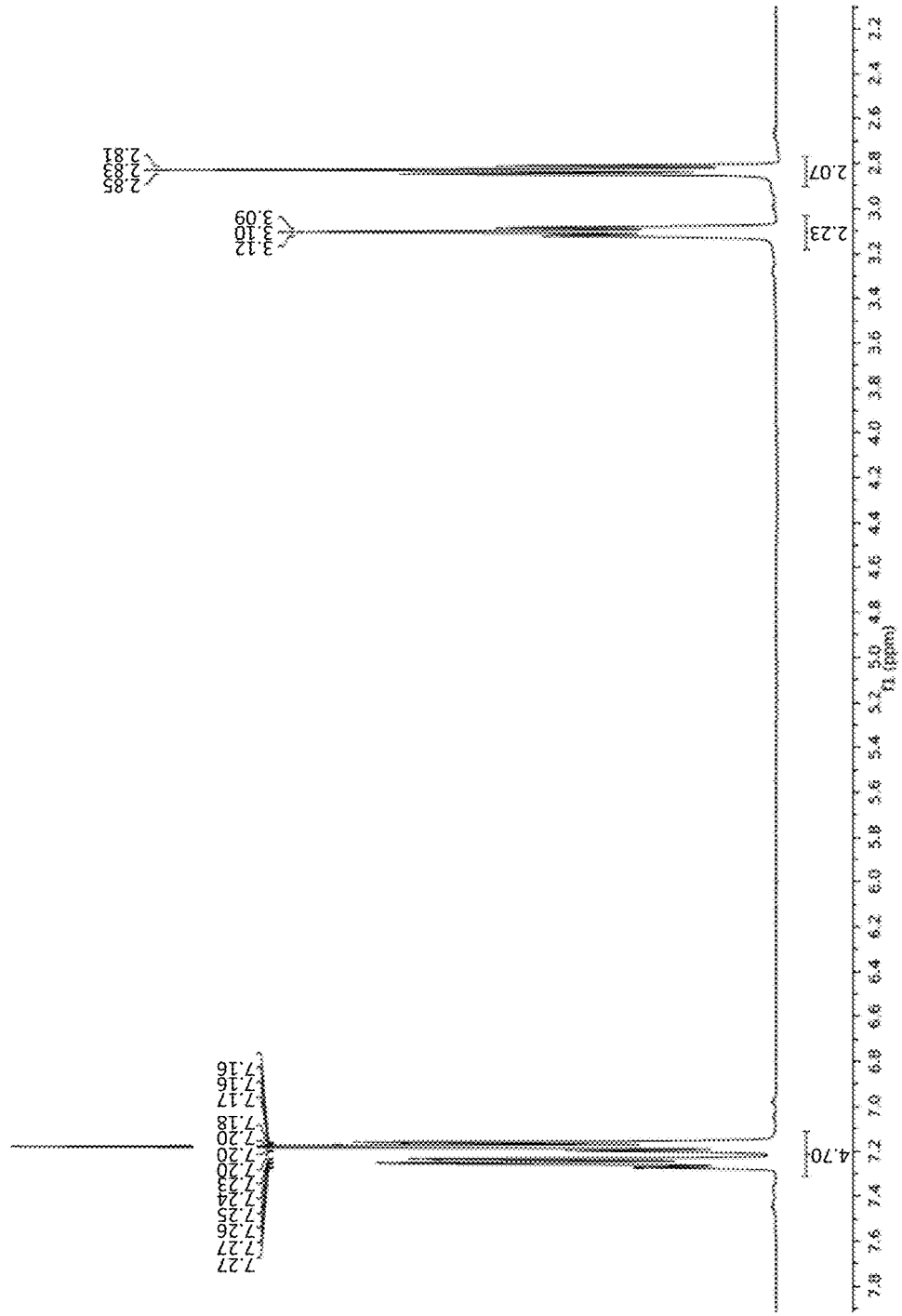
FIGS. 6A-B illustrate HNMR data of phenethylamine HCl (FIG. 6A) carvacrol (FIG. 6B) noting excellent purity.
Figure 6B:
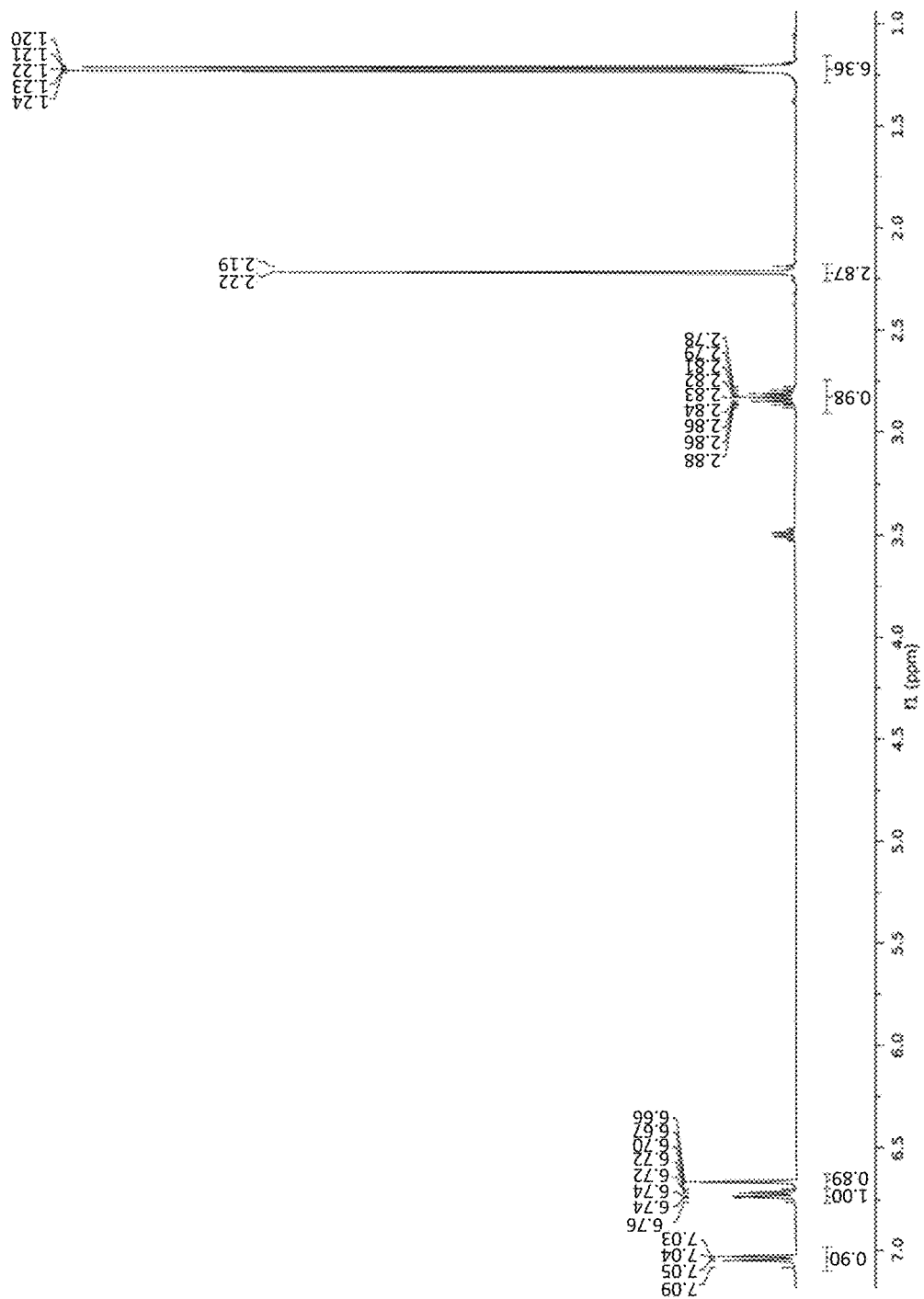

To illustrate generality of this conversion, three structurally diverse amino acids (phe, val, and his) were decarboxylated and isolated according to the methods described in Example 1 above, but with careful attention to purity and yield of carvacrol rather than recovery of carvone catalyst. The results of these experiments are summarized in Table 3. HNMR of product amine hydrochloride salts in $D_2O$ and corresponding carvacrol HNMR in chloroform-d are given in FIGS. 6A-B for a typical experiment demonstrating greater than 99% purity for both amine hydrochloride salt and carvacrol with no additional purification. All experimental protocols (amounts, time, temperatures etc.) are the same as for Example 1, except that it was found that carvacrol could be isolated neat from the partitioned acidic aqueous layer after isomerization with no need for ether or other organic solvent extraction. Thus, for all figures illustrating carvacrol purity, carvacrol was obtained by removing the aqueous layer from partitioned carvacrol in a separatory funnel.

TABLE 3

| Amino Acid | % Yield Amine HCl Salt | % Yield Carvacrol | % Purity GC + HNMR |
|---|---|---|---|
| val | 81 | 97 | >99 |
| phe | 77 | 97 | >99 |
| his | 88 | 93 | >99 |

Figure 7A:
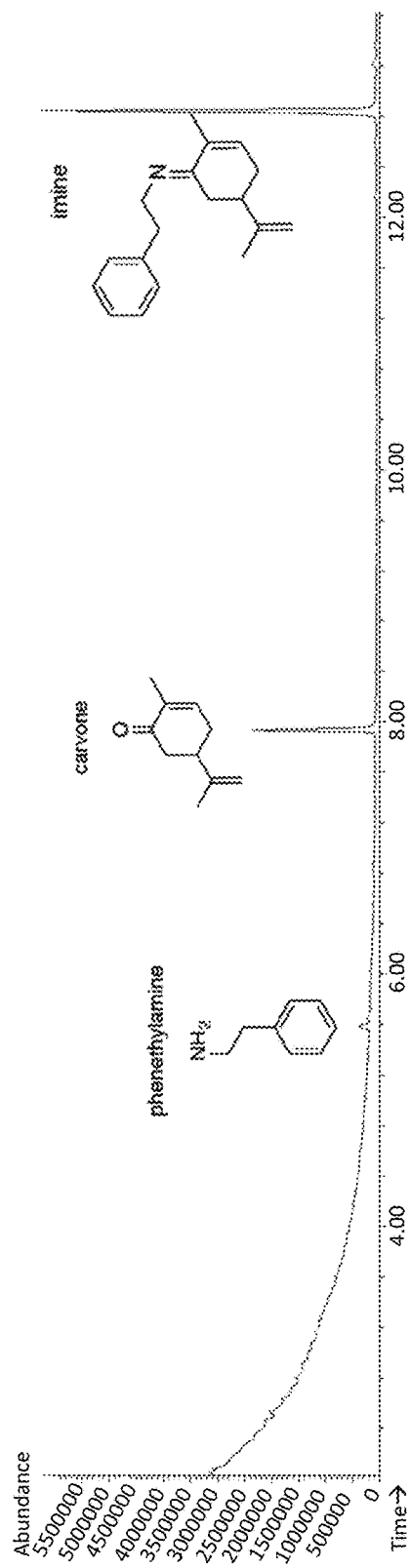
FIG. 7A illustrates a gas chromatograph (GC) of an embodiment of a reaction mixture of the present disclosure with carvone immediately following decarboxylation of phenylalanine. From left to right are the signals of free phenethylamine (m/z=121), carvone (m/z=150), and the imine of these two species (m/z=253).
Figure 7B:
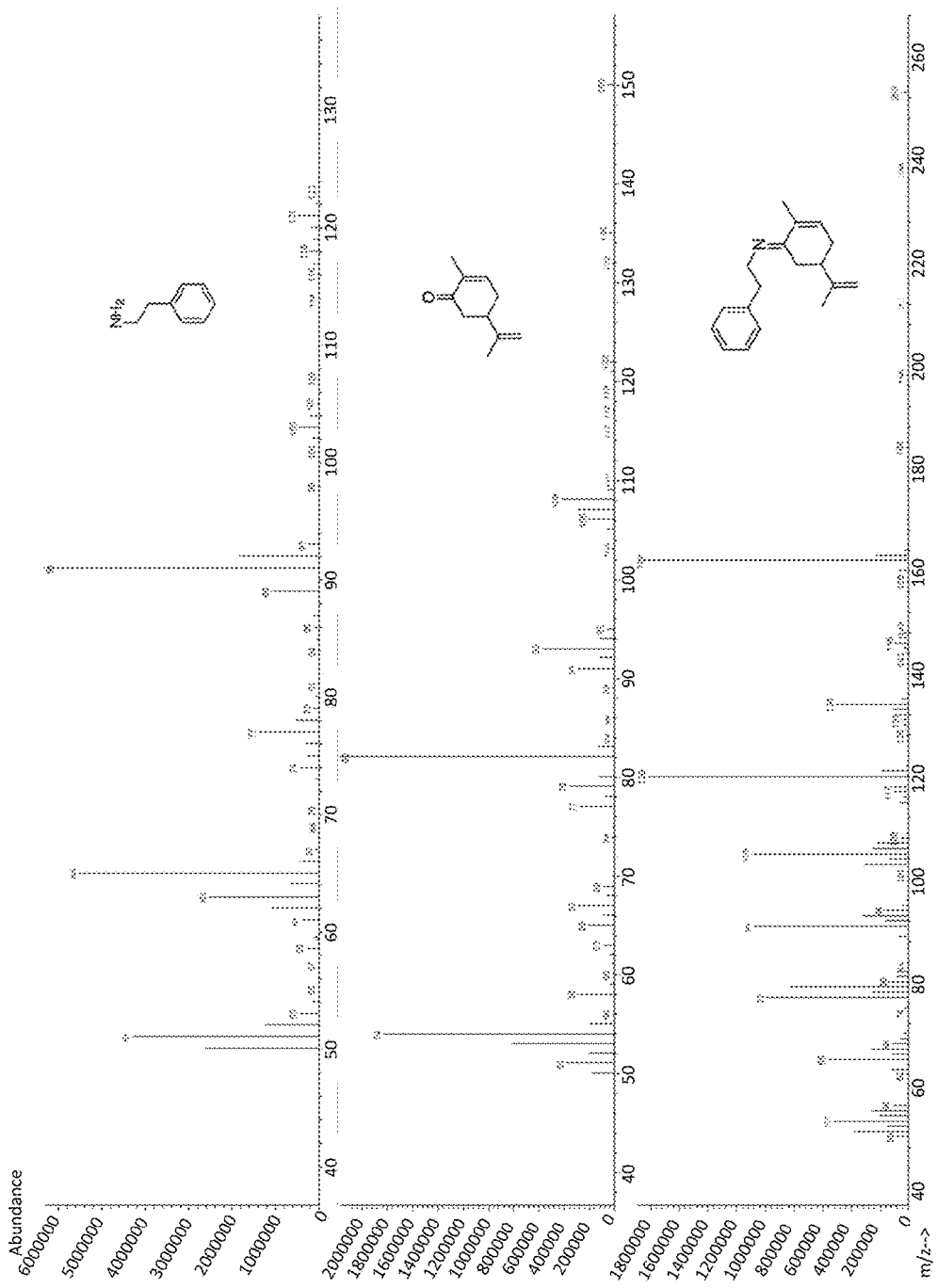
FIG. 7B illustrates mass spectroscopy data for each gas chromatograph signal from FIG. 7A, illustrating the identity of each peak.
Figures 9A, 9B:
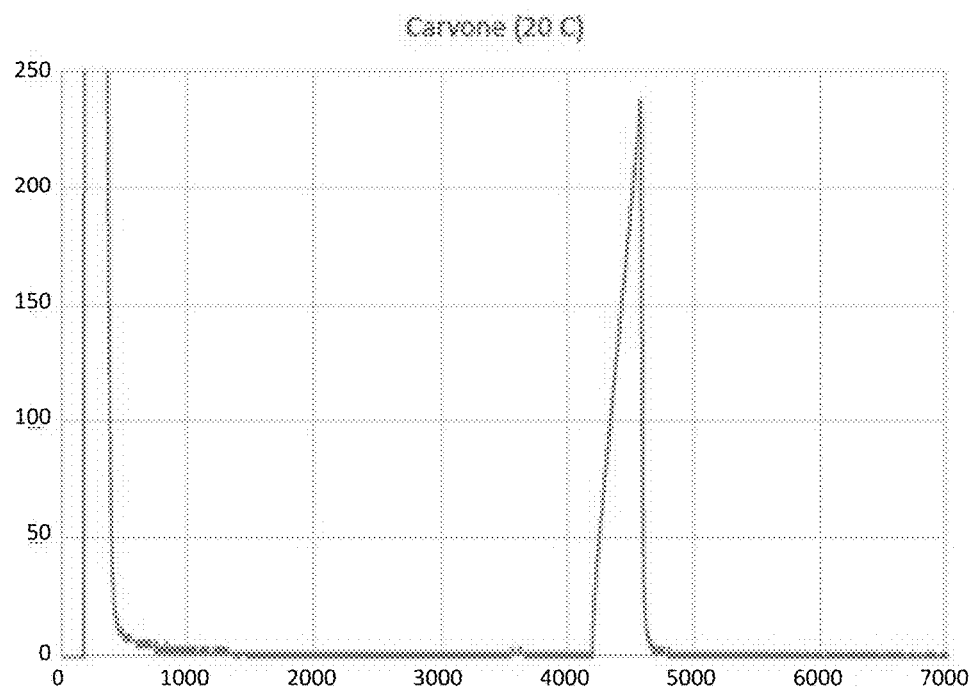
FIGS. 9A-D illustrate GCs depicting conversion of pure carvone (9A) to pure carvacrol (9D) during hydrolysis of imine in aqueous acid (with FIGS. 9B and 9C illustrating intermediates between 9A and 9D). Conversion occurs over a 5 minute interval.
Figure 9C:
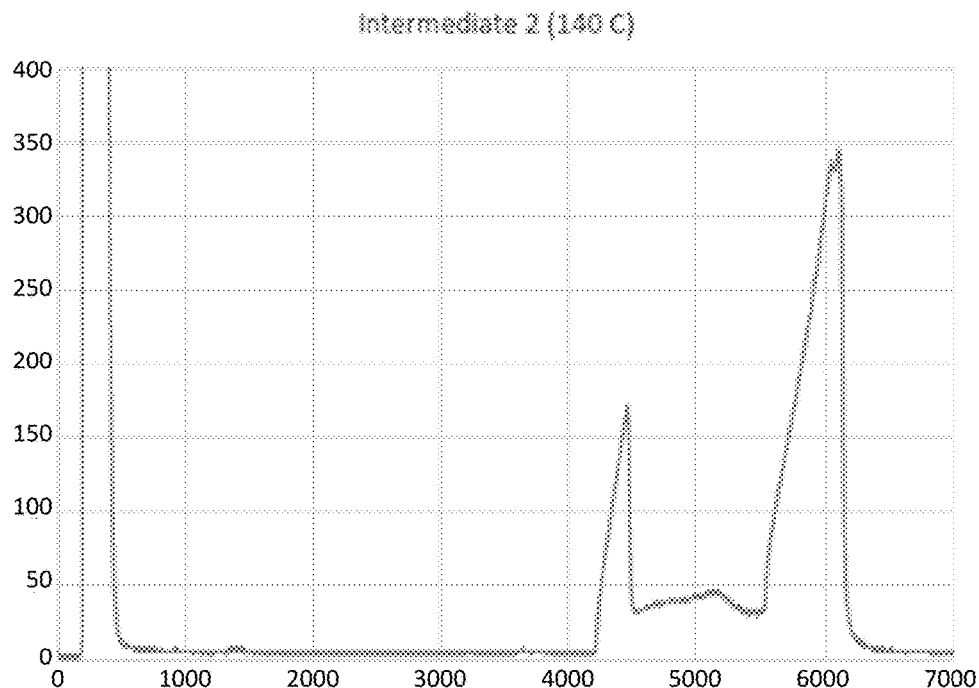
Figure 9D:
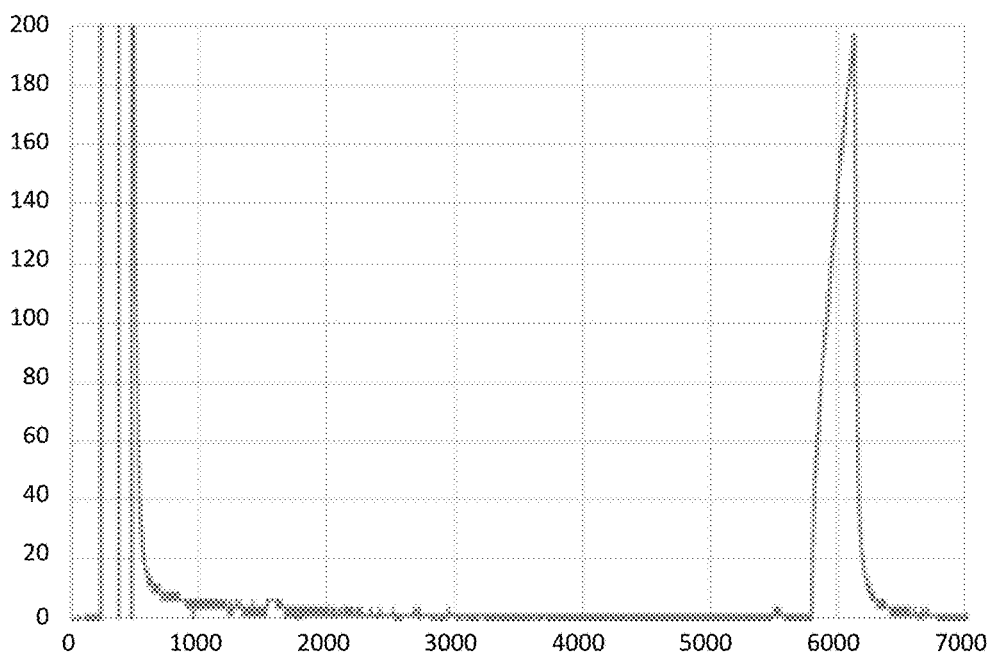

Gas chromatographic data in FIG. 7A illustrates the status of the reaction mixture immediately following initial heating and completed decarboxylation. Note the presence of the decarboxylated imine of phenethylamine with carvone as the predominant species compared to free amine. Mass spectroscopy data in FIG. 7B accompany each GC signal, illustrating the identity of each peak. FIGS. 8A-B show the status of the system as acidic aqueous hydrolysis is begun at low temperature (too low of a temperature to isomerize carvone to carvacrol).

If desired, instead of recovering carvone after hydrolysis, carvone may be isomerized to useful byproduct carvacrol by conducting acidic aqueous hydrolysis at higher temperatures (e.g., temperatures above about 180° C.). Not only does the conversion drive the process to greater yield and purity of the product amine, but also generates the oil of oregano (carvacrol) byproduct. FIGS. 9A-D illustrate the progress of completing the isomerization using gas chromatogram data over the course of the acid hydrolysis step.

Figure 10:
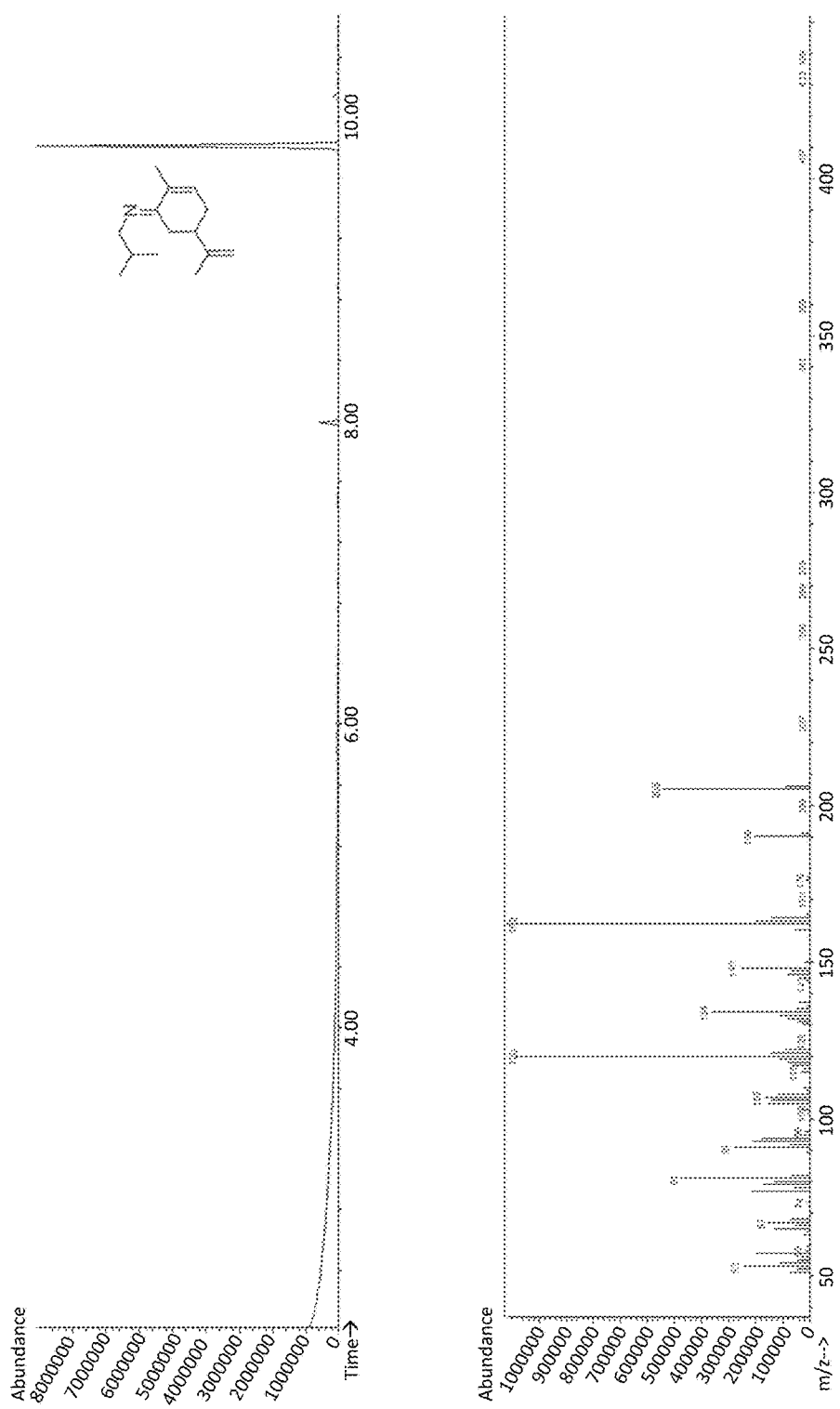
FIG. 10 is a GC of purified imine of valine decarboxylation showing ~5% carvone impurity and no free amine.
Figure 11:
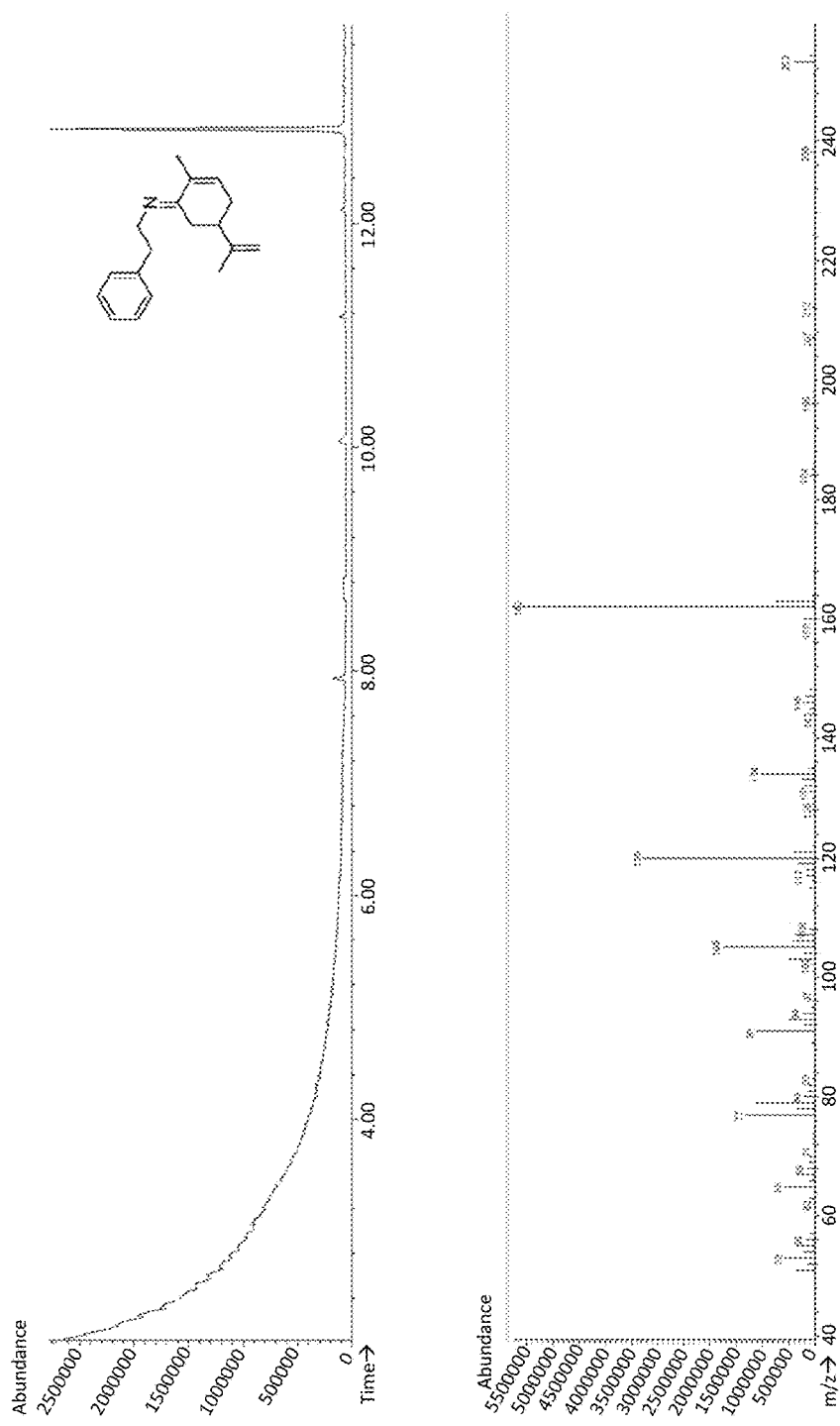
FIG. 11 illustrates a GC of purified phenethylamine imine showing ~5% carvone impurity and no free amine.
Figure 12A:
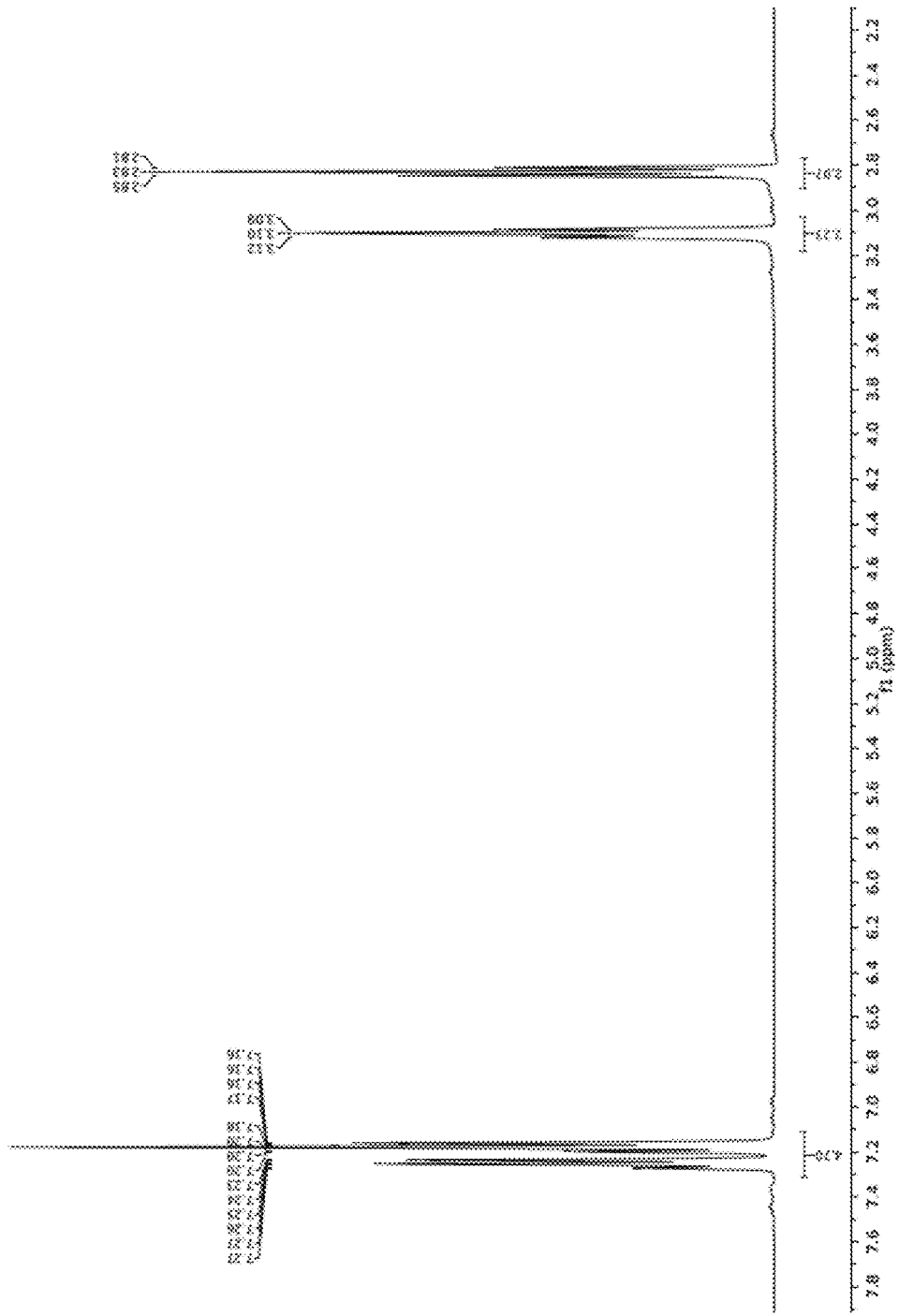
FIGS. 12A-12F illustrate HNMR data of phenethylamine HCl for crude decarboxylation products with the catalysts carvone (12A), citral (12B), β-ionone (12C), R-pulegone (12D), and 3-methylcyclohex-2-enone (12E), and dihydrocarvone (12F). R-carvone (12A) achieves >99% purity without additional purification via recrystallization from 1-propanol.
Figure 12B:
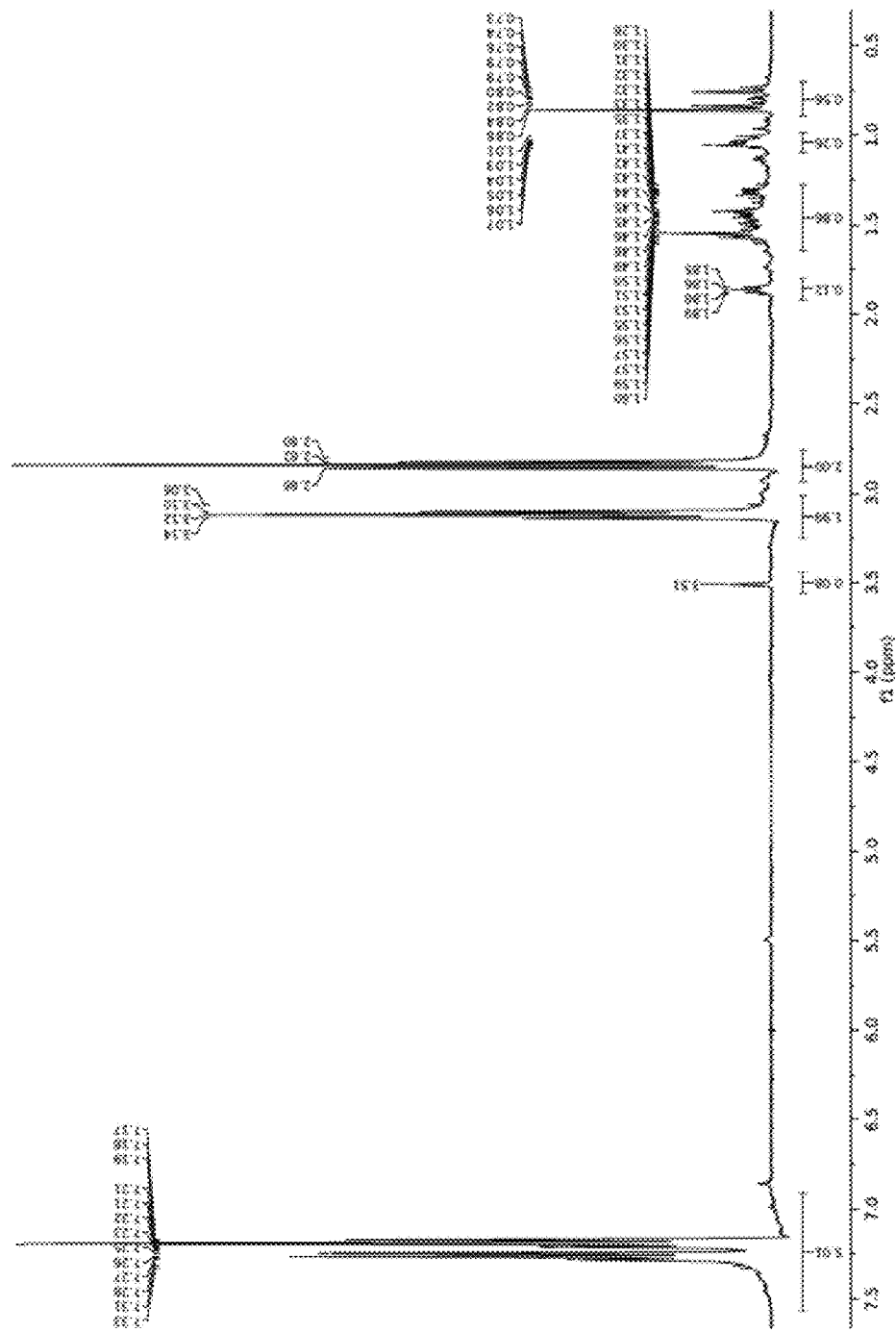
Figure 12C:
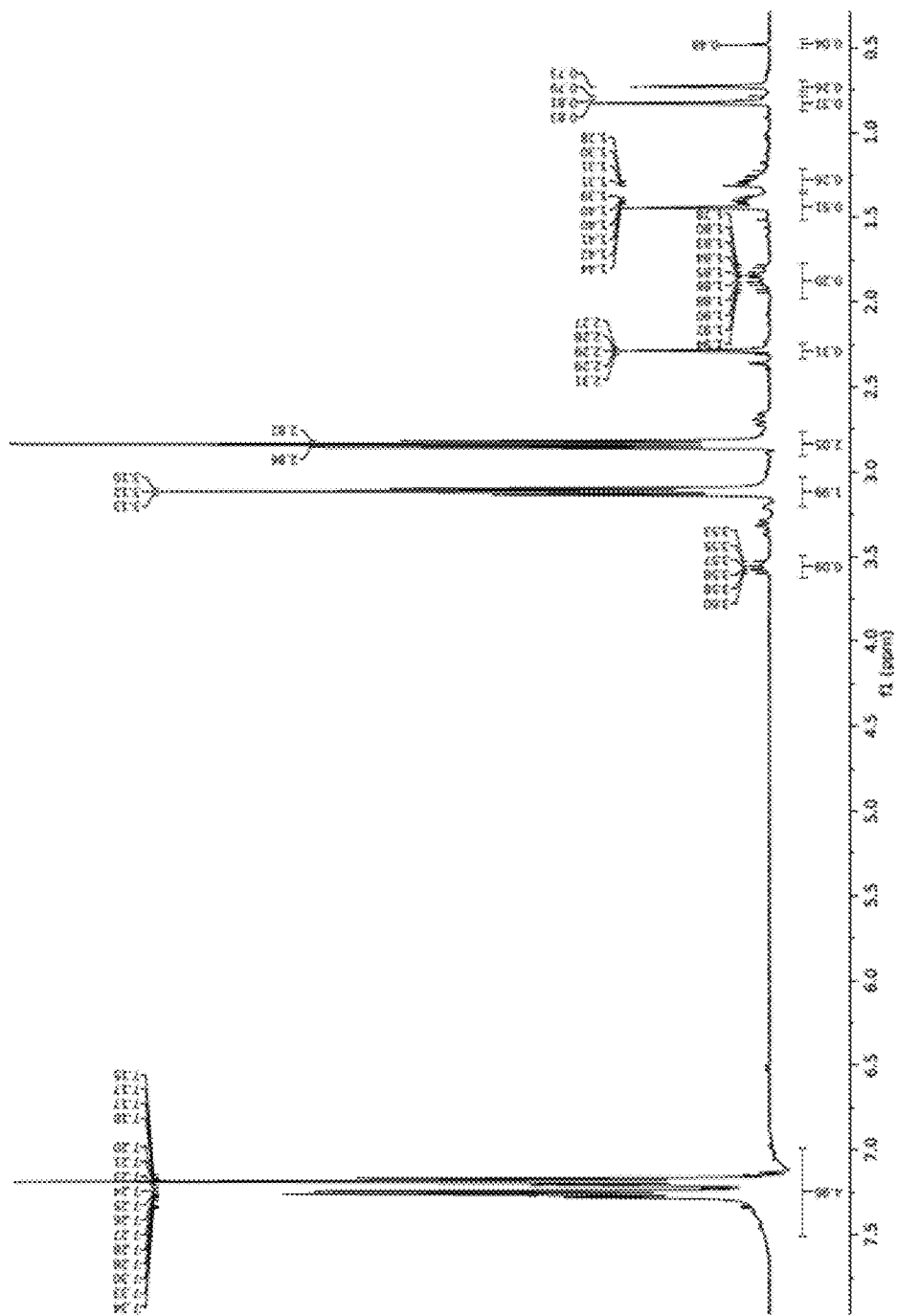
Figure 12D:
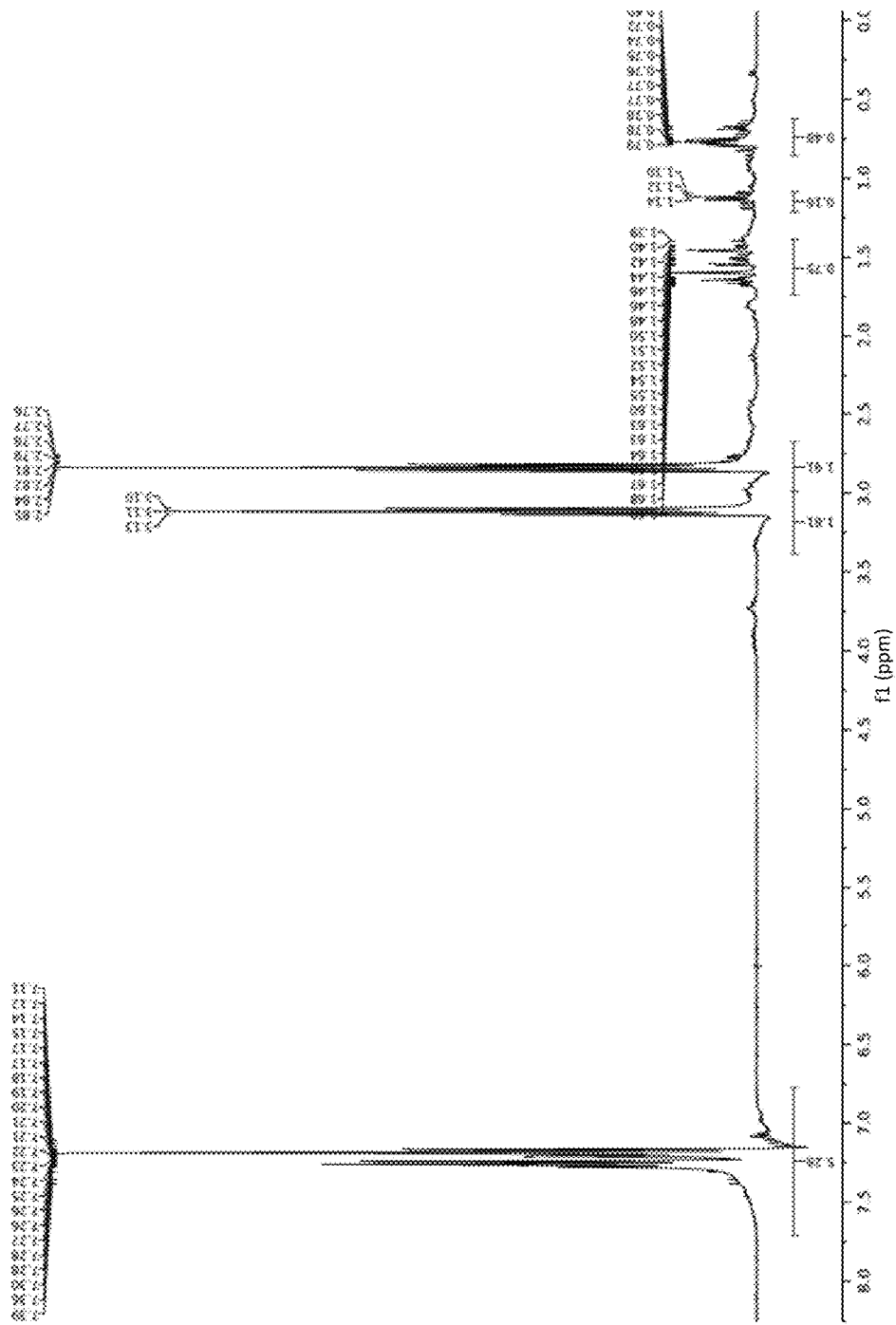
Figure 12E:
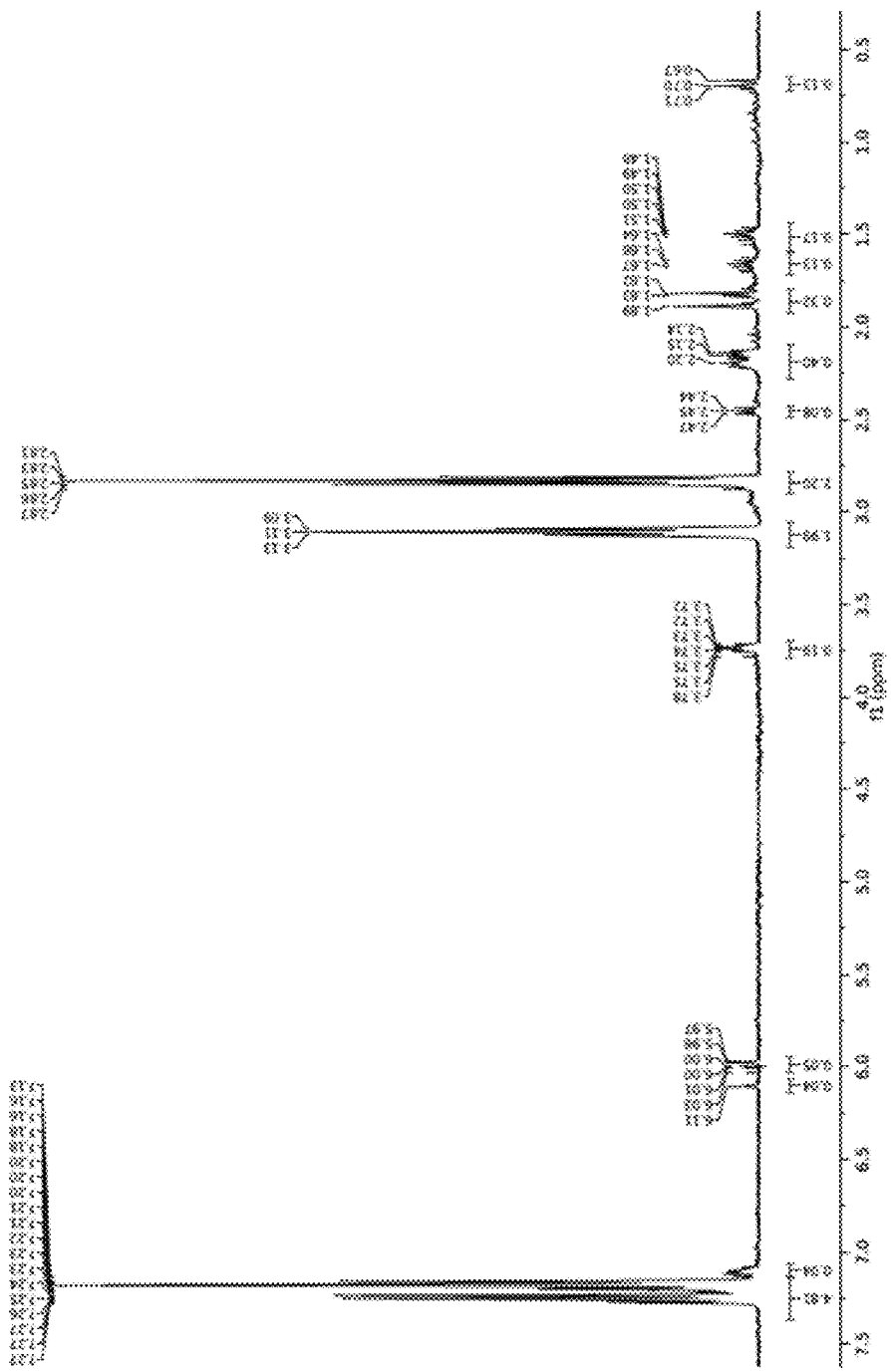
Figure 12F:
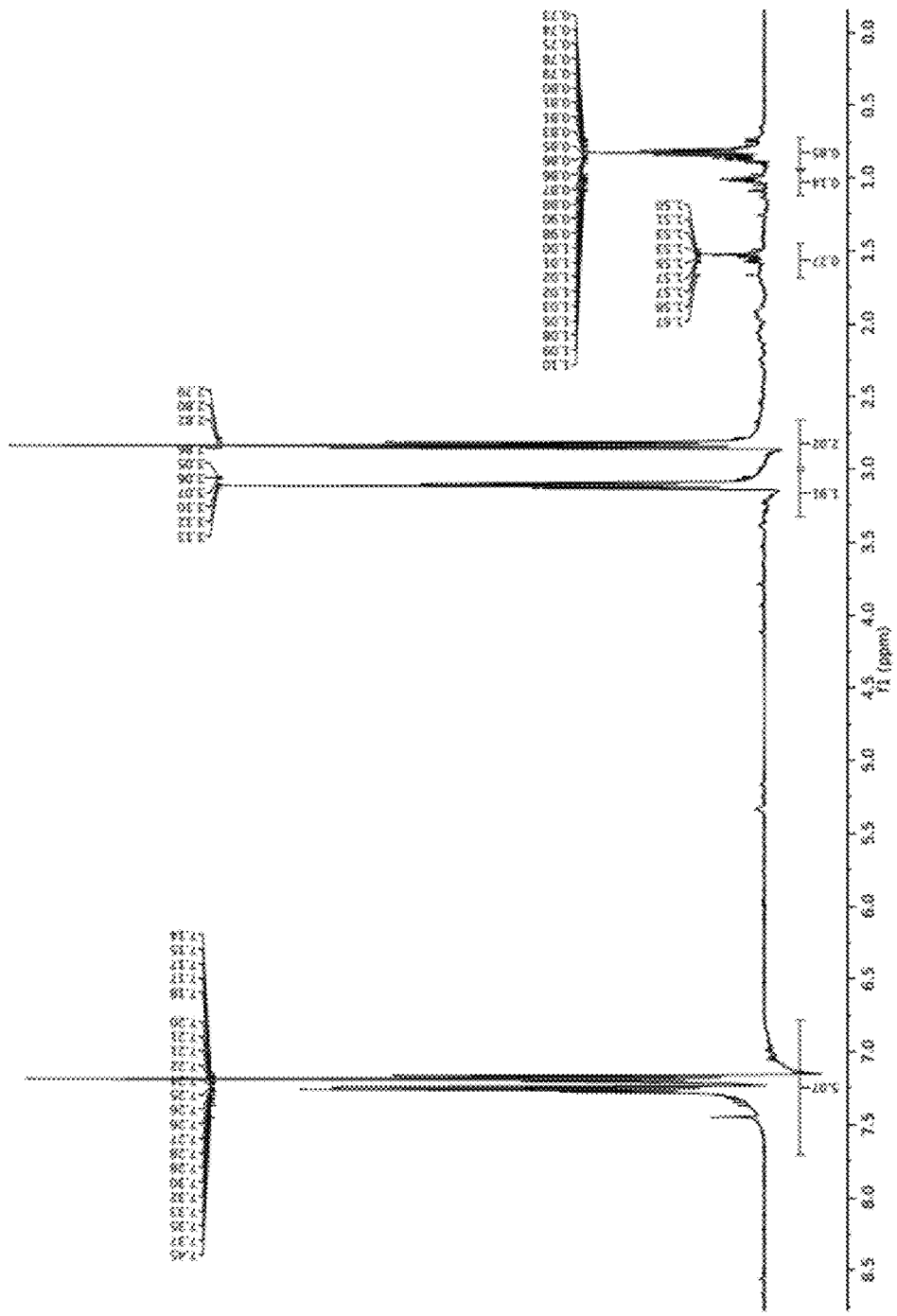
Figure 13:
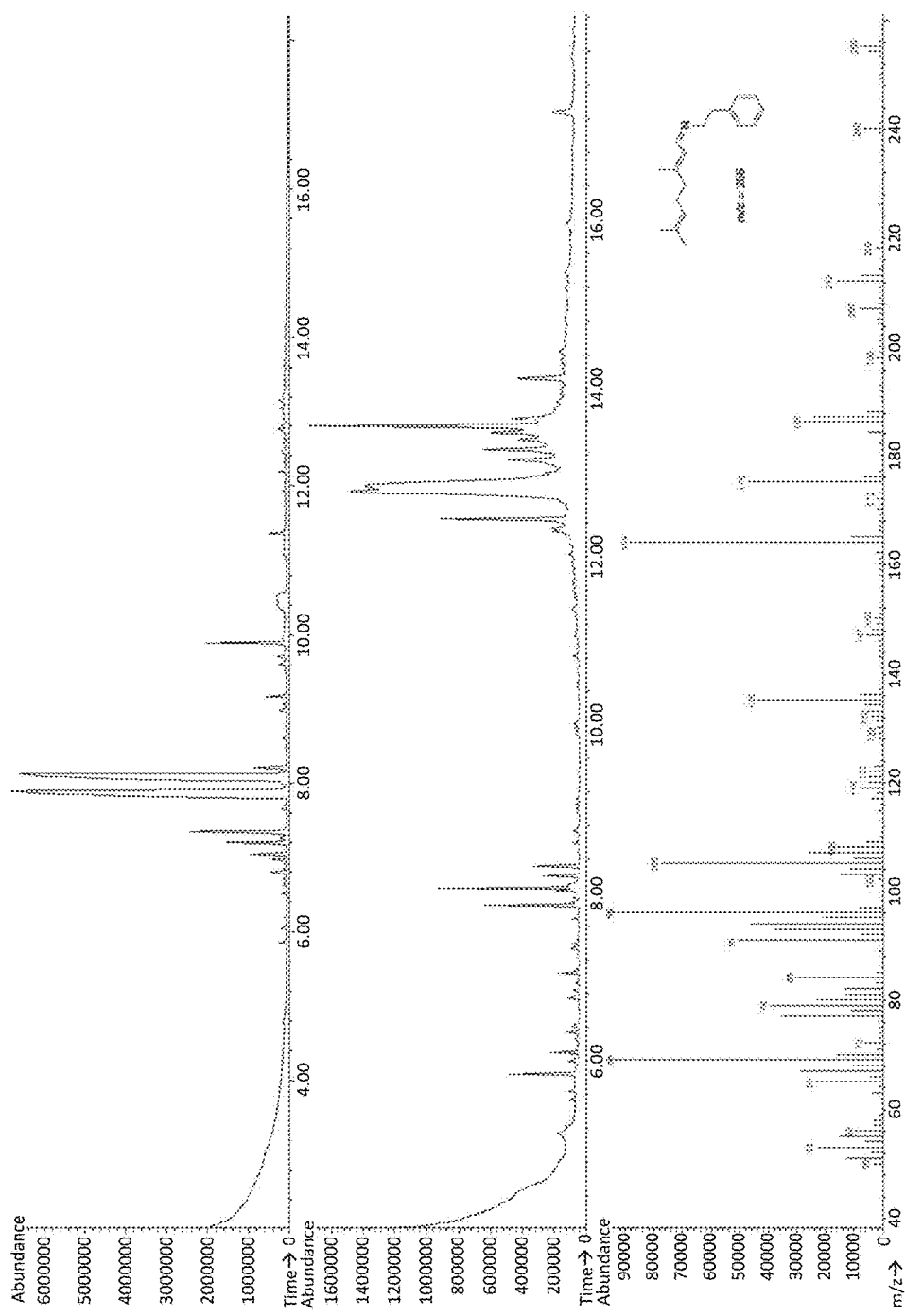
FIGS. 13-17 illustrate gas chromatographic data and mass spec data for each of the catalysts citral (FIG. 13), β-ionone (FIG. 14), R-pulegone (FIG. 15), and 3-methylcyclohex-2-enone (FIG. 16), and dihydrocarvone (FIG. 17). For each figure, the top panel shows CG data for the supplied catalyst, middle panel shows GC of the reaction mixture immediately following decarboxylation of phenylalanine, and bottom panel is MS for the middle GC panel for each catalyst illustrating the identity of each peak.
Figure 14:
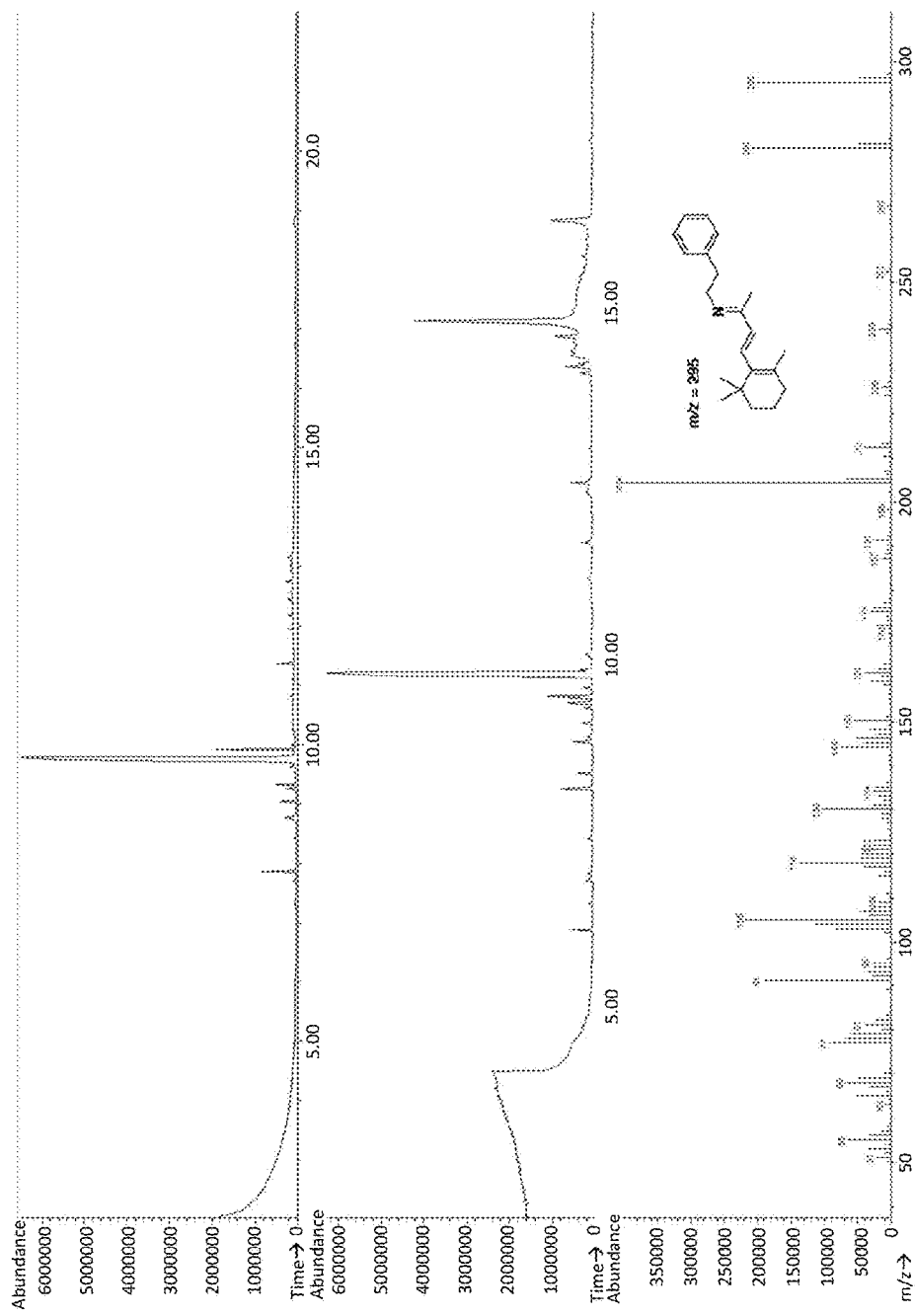
Figure 15:
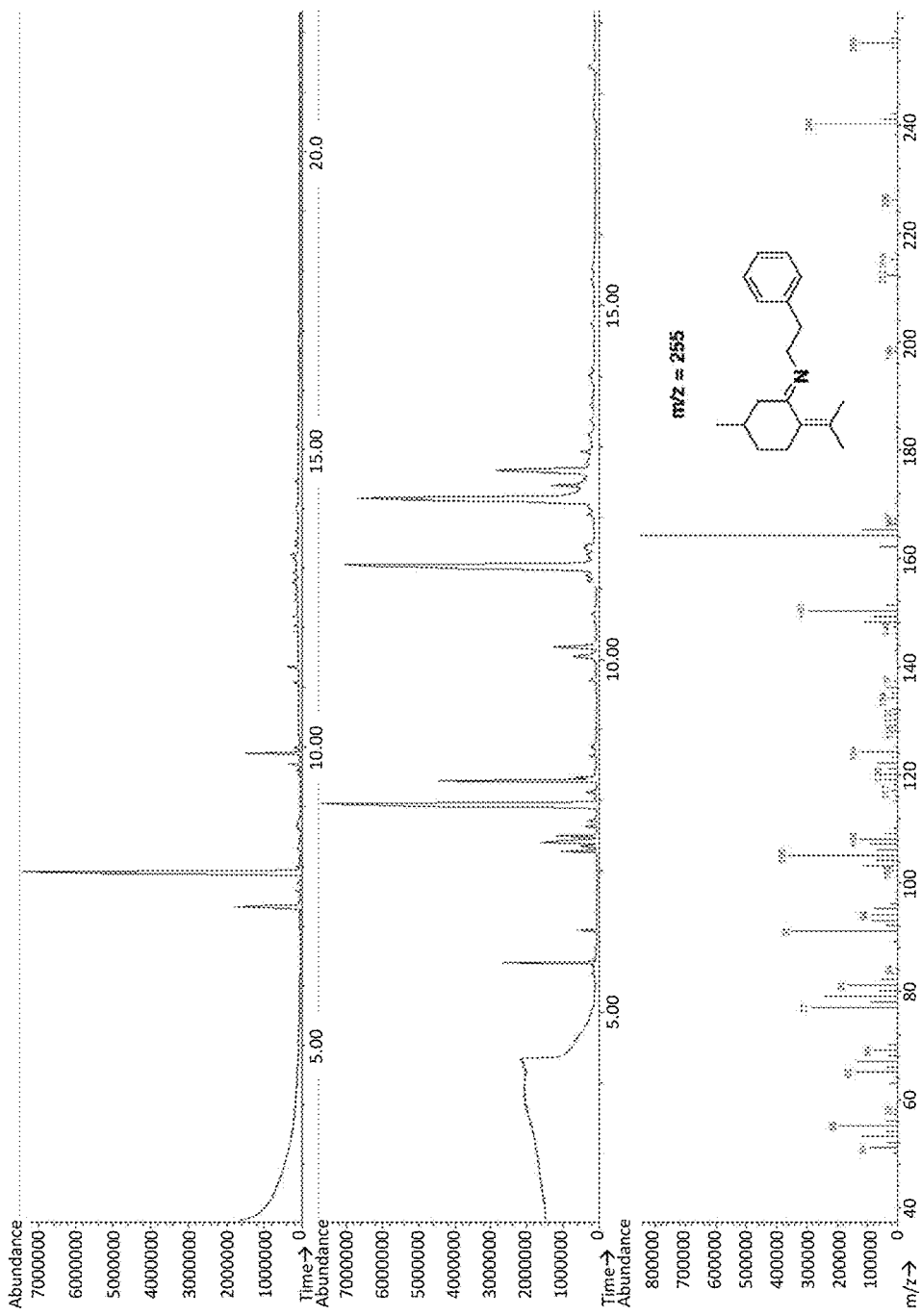
Figure 16:
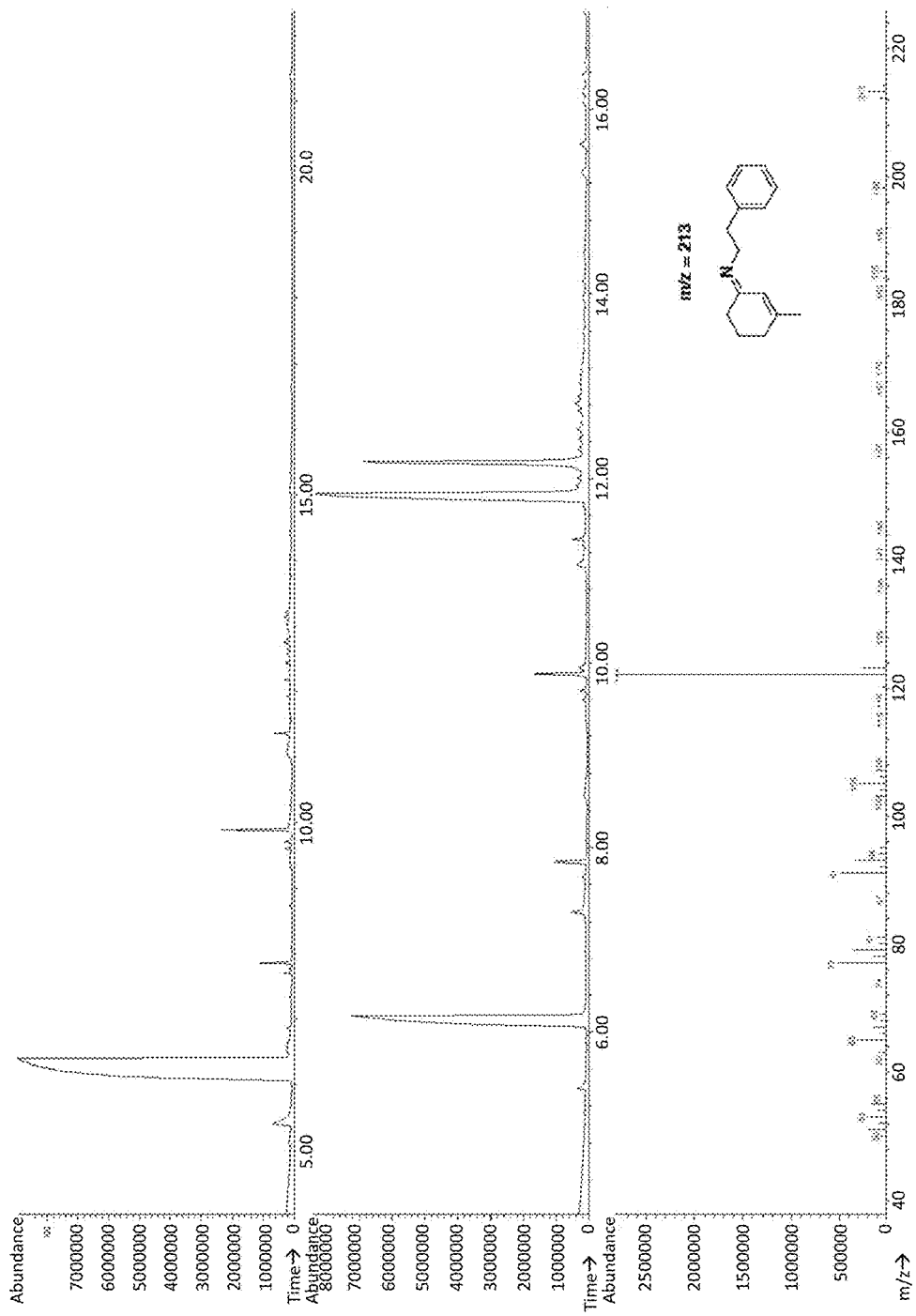
Figure 17:
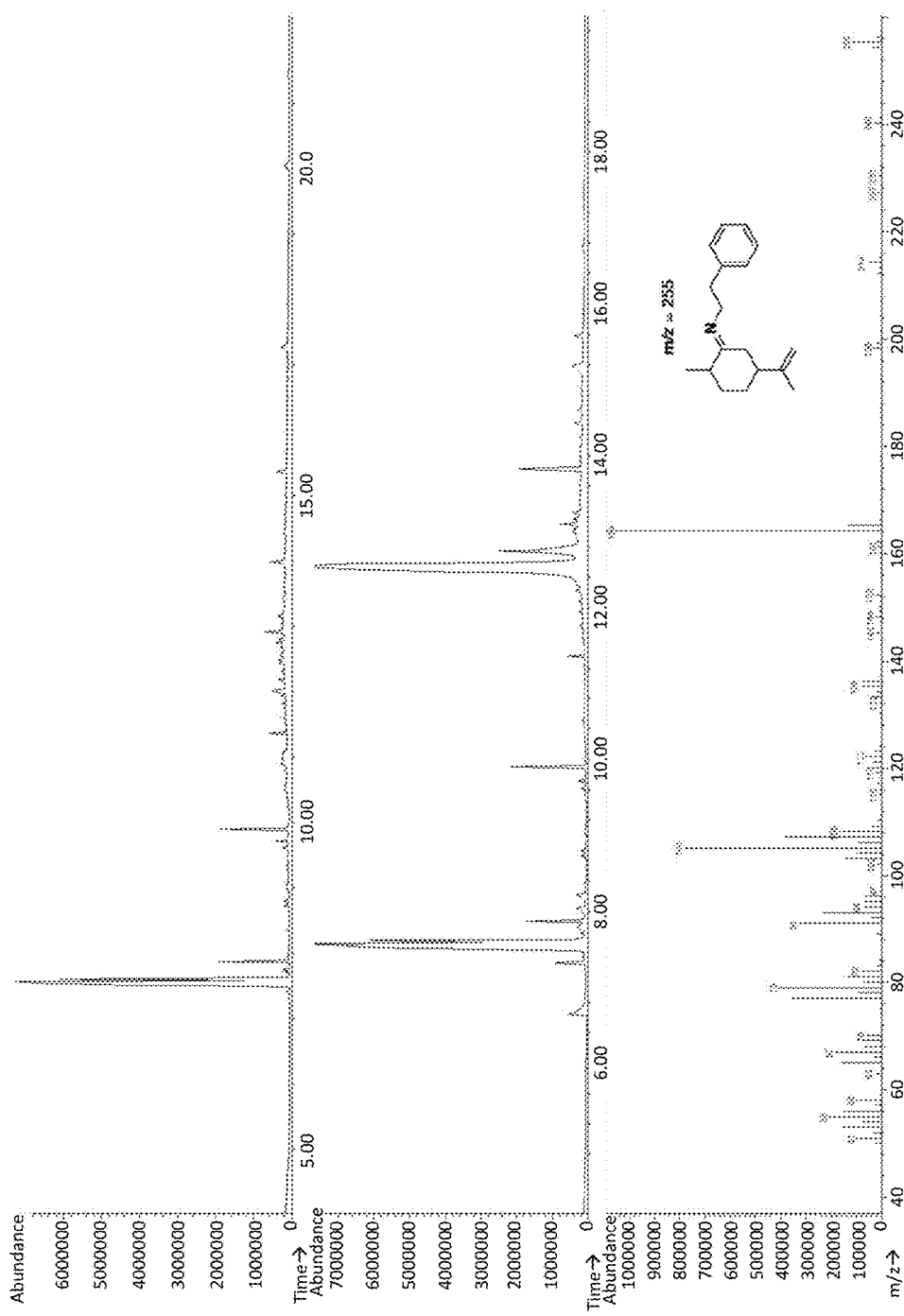

Additionally, if desired, the imine of most decarboxylation products may be stored over 3 angstrom molecular sieves, rather than hydrolyzing the imine in aqueous acid. FIGS. 10 and 11 depict gas chromatograms of the imines of valine and phenylalanine, decarboxylation products with minor carvone impurity. To get the highest purity of imine possible, the catalyst load was reduced to equimolar in order to negate the need for removal of excess catalyst. The reaction mixture after the first heating (including reaction solvent, trace amine, trace catalyst, and imine) was dried over 3 angstrom molecular sieves to remove all trace water formed from condensation of residual amine and catalyst, forming the pure imines demonstrated by the GC-MS chromatograms in FIGS. 10 and 11. The imines are stable when stored in this solution at room temperature.

Example 3—Additional Enone Catalysts for Decarboxylation of Amino Acids

This example describes experimental evidence demonstrating the use of various enone catalysts in the decarboxylation of amino acids. Evidence of the imine intermediate of each decarboxylation as well as the purity of the recovered catalysts are demonstrated via GC-MS data in the figures. Purity of the recovered product amine hydrochloride salts is also shown via HNMR data. In general, decarboxylation rates of the enones are similar to carvone, achieving elimination of carbon dioxide in less than 5 min as the reaction vessel is heated to 190° C.

Methods and Results

To illustrate use of multiple enone catalysis in the methods of the present disclosure for decarboxylation of amino acids, the enones citral, α-ionone, β-ionone, R-pulegone, verbenone, and 3-methylcyclohex-2-enone were used as catalysts in the decarboxylation of phenylalanine according to the procedures described above in Example 1. Additionally, the ketone dihydrocarvone was investigated, given its structural similarities to carvone and known isomerization reaction to the enone, carvenone. Carvenone serves as an effective catalyst and useful byproduct. The structures of the tested enone catalysts are shown below, with carvone structure provided as reference.

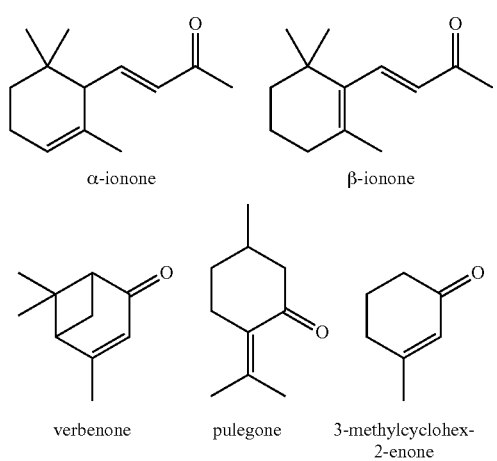

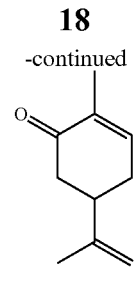

carvone

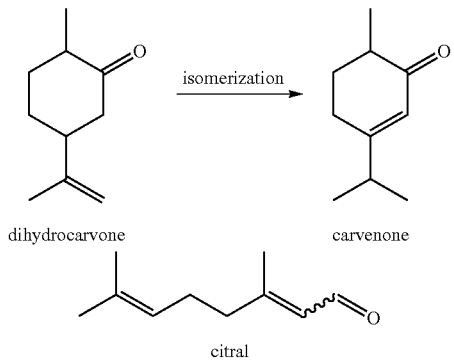

dihydrocarvone    carvenone citral

The results of these experiments are summarized in Table 4. HNMR of product amine hydrochloride salts in $D_2O$ and corresponding carvacrol HNMR in chloroform-d are given in FIGS. 12A-F for a typical experiment demonstrating greater than 80% purity for amine hydrochloride salt with no additional purification.

TABLE 4

Survey of Enone Catalysts for Decarboxylation of Phenylalanine

| Catalyst | % Yield Amine HCl Salt | % Catalyst Recovered | % Amine HCl salt Purity (initial) |
| --- | --- | --- | --- |
| citral | 36 | 0 | 83 |
| α-ionone* | — | — | — |
| β-ionone | 88 | 81 | 82 |
| R-pulegone | 93 | 93 | 87 |
| verbenone* | — | — | — |
| 3-methylcyclohex-2-enone | 96 | 60 | 86 |
| dihydrocarvone | 84 | 82** | 88 |
| R-carvone | 76 | 97 | >99 |

*decompose during reaction preventing product isolation
recovered as carvenone after isomerization Gas chromatographic data and Mass spec data for each of the catalysts is provided in FIGS. 13-17. The top panel in each figure is a GC of the supplied catalyst (including a mixture of isomers). The middle panel is a GC illustrating the status of the reaction mixture immediately following initial heating and completed decarboxylation. Note the presence of the decarboxylated imine of each enone catalyst with phenethylamine as the predominant species compared to free amine. The bottom panel in each figures shows mass spectroscopy data to accompany each GC signal for after decarboxylation, illustrating the identity of each peak. Citral, pulegone, and dihydrocarvone are essential oils obtained from the supplier as mixtures of diastereomers. The multiple peaks observed are imines with the multiple enone stereoisomers. The presence of these imine peaks further demonstrates that expensive stereospecific and purified catalysts are not necessary to achieve decarboxylation. It is of note that pulegone (FIG. 15**) partially decomposes during decarboxylation to produce an m/z=215 byproduct at 11.3 min in the chromatogram.

Figure 18A:
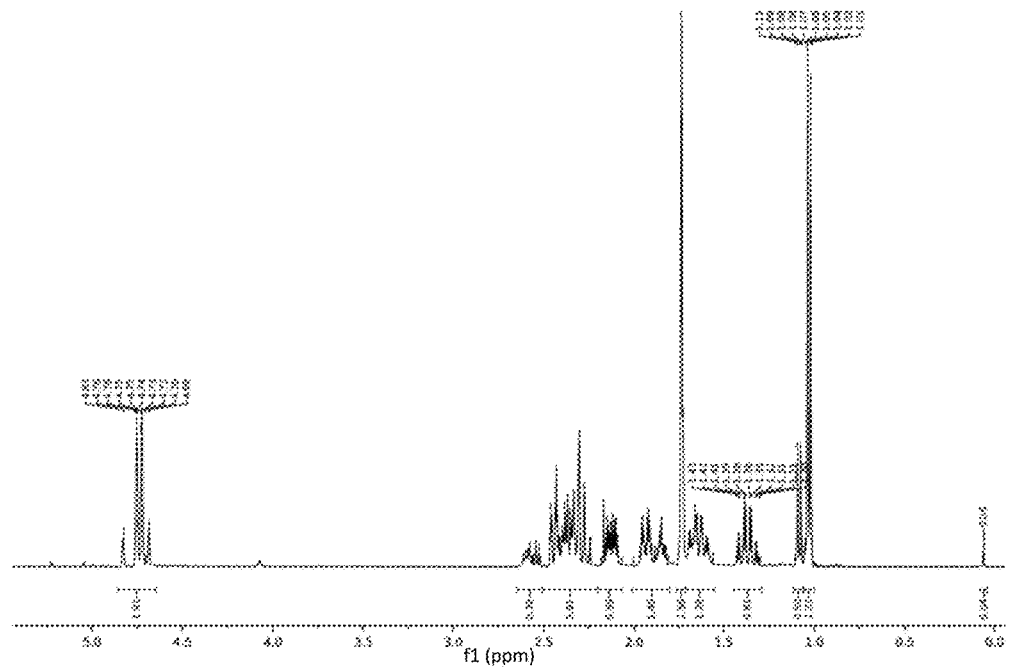
FIGS. 18A-18B illustrate isomers dihydrocarvone (18A), having 2 vinyl diastereotopic protons giving 2 vinyl protons as depicted, and carvenone (18B) having just one. Spectra conform to published standards.
Figure 18B:
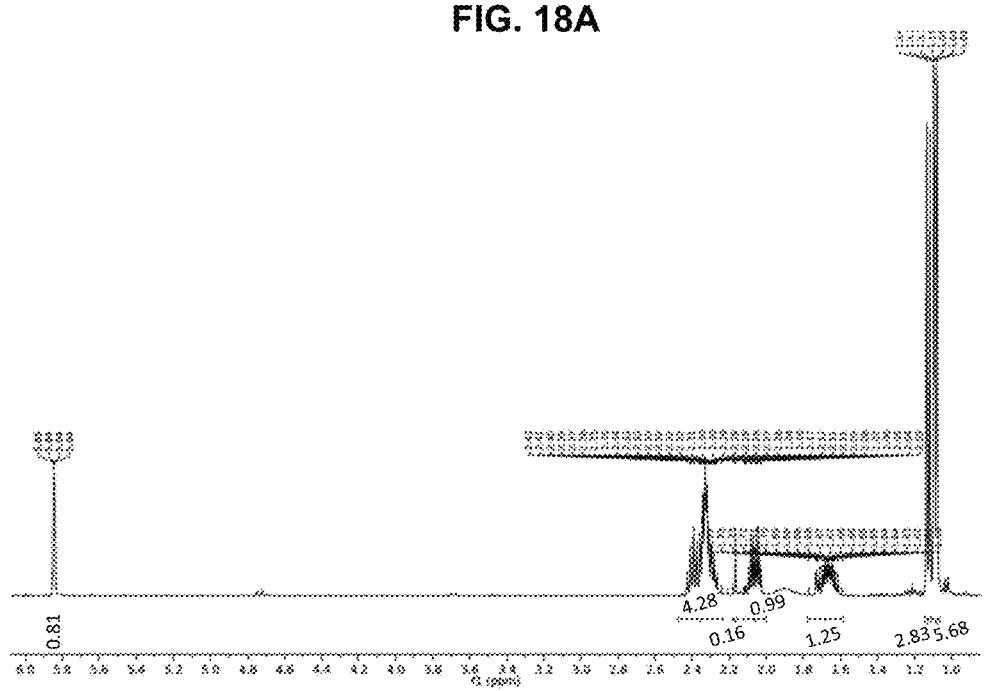

Hydrolysis of the imine intermediates to product amine hydrochloride salts proceeds as with R-carvone in Examples 1 and 2. Heating to a temperature of greater than 80° C. in aqueous HCl facilitates hydrolysis of imines. Catalysts partition with the aqueous layer and can be recovered neat or extracted with a typical organic solvent with a couple of notable exceptions. Citral decomposes upon hydrolysis. Dihydrocarvone isomerizes to carvenone, a more stable enone, during hydrolysis, as illustrated in FIGS. 18A-18B (similar to isomerization of carvone/carvacrol described in Example 2, above). The carvenone recovered is also ideally suited for the decarboxylation process and should be considered a useful byproduct.

CONCLUSION

The data presented in the present example support the broad efficacy of enone catalysis for the decarboxylation of amino acids. Of the catalysts surveyed, including those supplied as a mixture of isomers, decarboxylation rates were all similar in accomplishing the reaction in less than 5 min as the mixture was heated to a sufficient temperature. While carvone has the ability to isomerize in such a way (enone to phenol) that drives the imine hydrolysis equilibrium to completion resulting in the highest initial purity (>99%) of product hydrochloride salts, all catalysts result in at least 80% purity of the crude product, which may be further purified using common methods such as recrystallization. Of the catalysts surveyed, dihydrocarvone also shows the ability to isomerize to a useful by-product, which is recovered in good yield.

Figure 19:
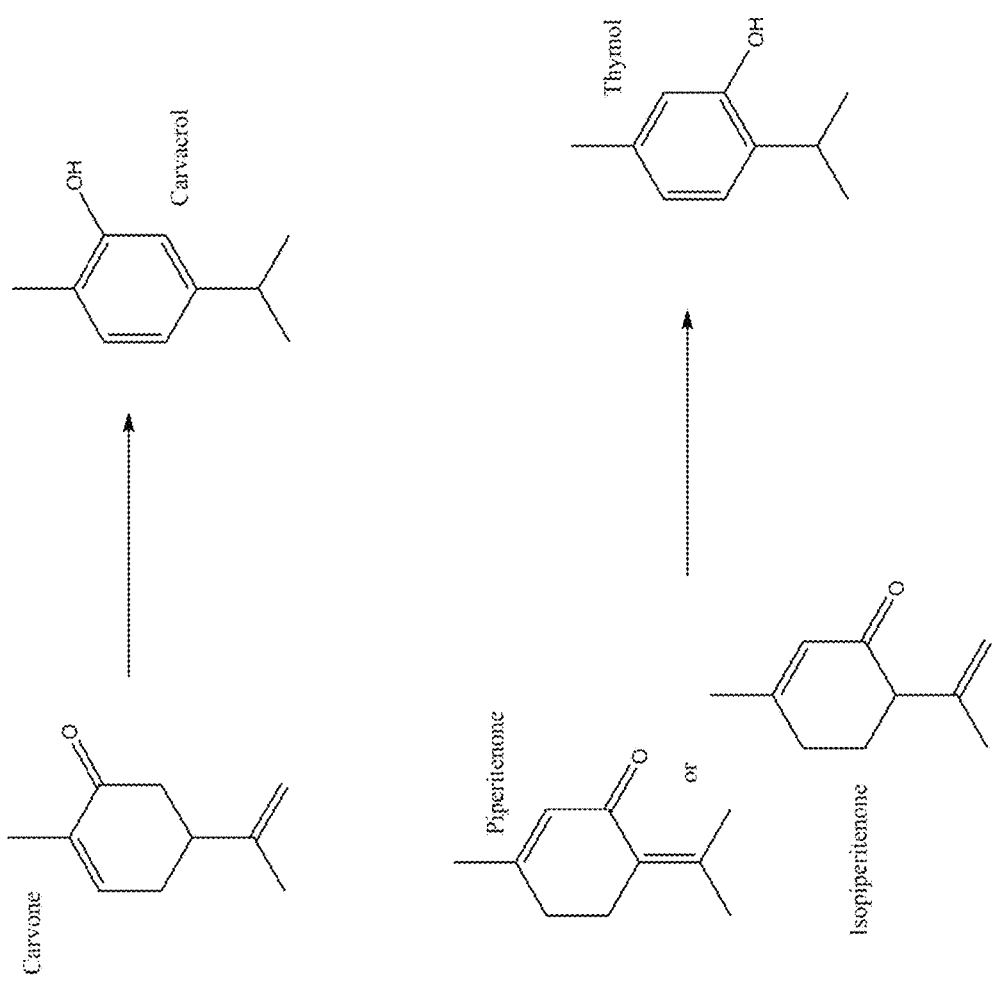
FIG. 19 illustrates isomerizations to produce carvacrol and thymol.
Figure 20:
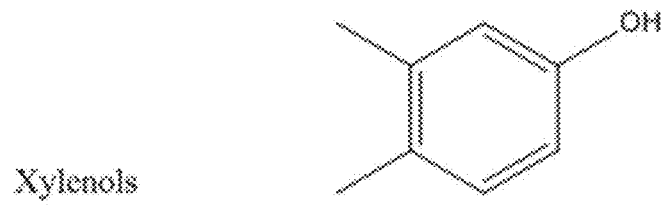
FIG. 20 illustrates chemical structures of some xylenol compounds and ethylmethylphenol compounds that can be produced as catalyst byproducts in embodiments of the methods of the present disclosure.
Figure 20:
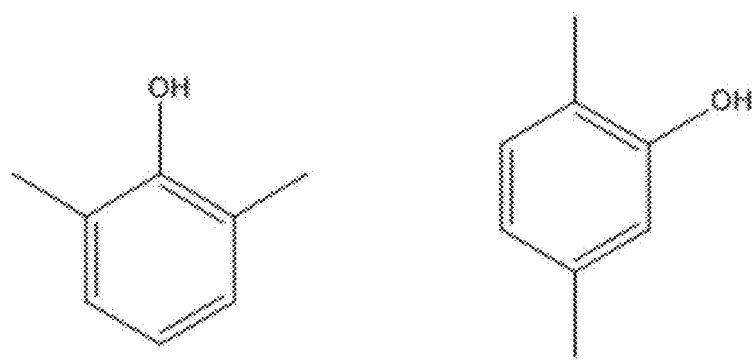
Figure 20:
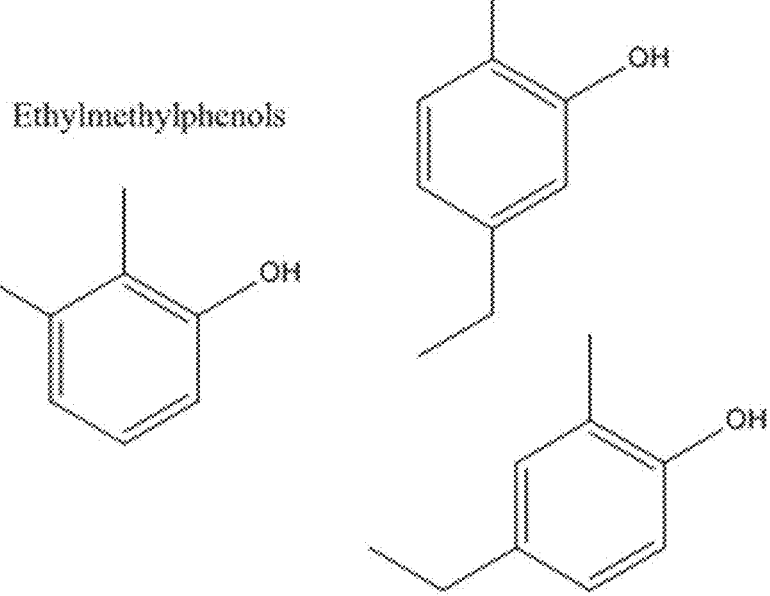
Figure 21:
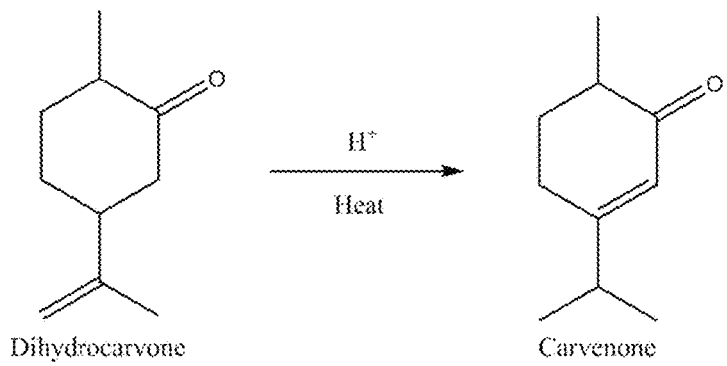
FIG. 21 illustrates acyclic and cyclic enal and enone analogs of carvenone (such as 2-pentenal, hex-3-en-2-one, piperitone, 3-ethyl-6-methylcyclohex-2-en-1-one, and 3-ethylcyclopent-2-ene-1-one) that can also be produced as catalyst byproducts in embodiments of methods of the present disclosure.
Figure 21:
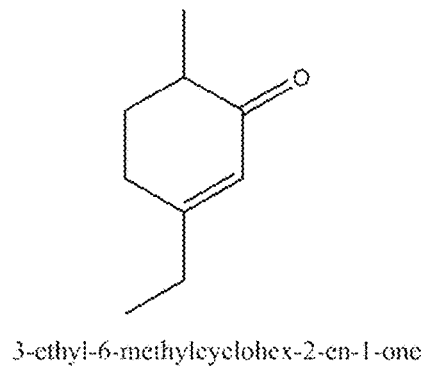
Figure 21:
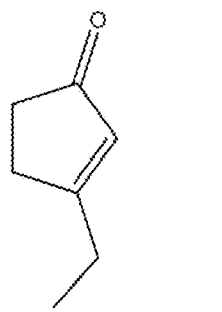
Figure 21:
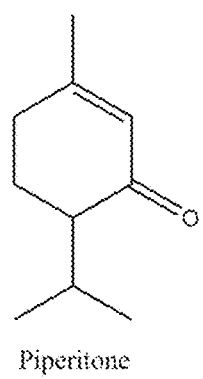
Figure 21:
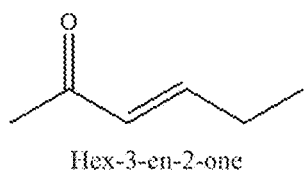
Figure 21:
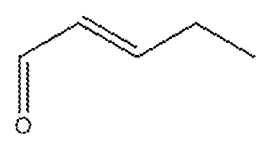

Other enone and/or ketone catalysts not tested in the present example can also have the ability to isomerize similar to dihydrocarvone and carvone to produce a useful byproduct. Such catalysts include enones such as piperitenone or isopiperitenone, which can isomerize to phenolic terpenes (such as thymol, see FIG. 19) and/or phenolic terpenoids. Other appropriate enone, enal, and/or ketone catalysts can isomerize to produce other phenolic terpenes and terpenoids, other phenolic structures, such as, but not limited to xylenols and ethylmethylphenols (see FIG. 20), and other acyclic and cyclic enals and enones, such as, but not limited to 2-pentenal, hex-3-en-2-one, piperitone, 3-ethyl-6-methylcyclohex-2-en-1-one, and 3-ethylcyclopent-2-ene-1-one (see FIG. 21).

REFERENCES each of the following references are incorporated herein by reference in their entirety.
1. Galat, A.; Friedman, H. L. *J. Am. Chem. Soc.* 1949. 71, 3976.
2. Hashimoto, M.; Eda, Y.; Osani, Y.; Iwai, T.; Aoki, S. *Chem. Lett.* 1986, 6, 893.
3. Yeh, W. L. et al.; 2002. U.S. Pat. No. 6,403,806 B1.
4. Martins, C. P. B., et al. *J. Chromatogr. A.* 2008, 1210, 115.
5. Omeis, M., et al. 2008. U.S. Pat. No. 7,485,756
6. Yaegashi, K., et al., 2009, EPO Patent: EP1586553

The invention claimed is:
1. A method for decarboxylation of amino acids to produce an amine via an imine intermediate, the method comprising:
(a) combining, in a pressurized reaction vessel, a mixture of an amino acid, a solvent, and a catalyst, the catalyst comprising a ketone, enone, enal, aldehyde, or combination thereof;
(b) heating the mixture at about 180° C., or more, for about 5 minutes, or more, wherein the amino acid is converted to its imine;
(c) cooling the reaction mixture from step (b) in the reaction vessel to a temperature below the boiling point of the solvent;
(d) adding an acid to the cooled reaction mixture from step (c) in the vessel; and
(e) heating the acid reaction mixture from step (d) to about 50° C., or more, to hydrolyze the imine to form an amine.

2. The method of claim 1, wherein the solvent is a short chain alcohol or water.

3. The method of claim 1, wherein the solvent is selected from the group consisting of: water, n-butanol, n-pentanol, isopropanol, ethanol, methanol, and n-propanol.

4. The method of claim 1, wherein the catalyst is selected from the group of ketones, enones, and enals consisting of: R-carvone, S-carvone, cyclohex-2-ene-1-one, acetophenone, 3-penten-2-one, butanone, dihydrocarvone, citral, β-ionone, R-pulegone, carvenone, cinnamaldehyde, 3-methylcyclohex-2-enone, pentadione, acetone, piperitone, poperitenone, isopiperitenone, methyl vinyl ketone, butenones, 2-phenylpropenal, and other R-ene-aldehydes.

5. The method of claim 1, wherein the catalyst is R-carvone, S-carvone, or mixture thereof.

6. The method of claim 1, wherein the catalyst is dihydrocarvone or carvenone.

7. The method of claim 1 when the amount of catalyst is from about 0.1 to about 2 mole equivalents.

8. The method of claim 1, wherein, in step (b), the mixture is heated in a microwave to a temperature of about 180° C. to about 190° C. and maintained at a temperature of about 180° C. to about 190° C. for about 5 min to about 10 min.

9. The method of claim 8, wherein the mixture is heated in a microwave to a temperature of about 190° C. for about 5 min, and if the reaction mixture is not clear after the 5 minutes of heating, the mixture is heated in the microwave to about 190° C. for about 5 to about 25 min longer.

10. The method of claim 1, wherein, in step (b), the mixture is heated in an oil bath at a temperature of about 180° C. to about 190° C. for about 5 min to about 20 min.

11. The method of claim 10, wherein, mixture is heated in an oil bath at a temperature of about 180° C. to about 190° C. for about 5 min, and wherein, if the reaction mixture is not clear after the 5 minutes of heating, the mixture is heated at about 180° C. to about 190° C. for an additional time of about 5 to about 20 min.

12. The method of claim 1, wherein the catalyst is a ketone, enone or enal capable of isomerization at temperatures of about 120° C., or more, to yield a byproduct selected from the group consisting of: enals, enones, phenolic terpenes, phenolic terpenoids, xylenols, and ethylmethylphenols.

13. The method of claim 12, wherein the acid reaction mixture during step (e) is heated to about 120° C., or more, to hydrolyze the imine to form an amine and to isomerize any unreacted catalyst.

14. The method of claim 12, wherein the catalyst byproduct is selected from the group consisting of: carvacrol, carvenone, thymol, xylenols, ethylmethylphenols, 2-pentenal, hex-3-en-2-one, piperitone, and 3-ehtyl-6-methylcyclohex-2-en-1-one, 3-ethylcyclopent-2-ene-1-one.

15. The method of claim 1, wherein the catalyst is S-carvone, R-carvone, or dihydrocarvone and wherein the acid reaction mixture during step (e) is heated to about 180°

C., or more, to hydrolyze the imine to form an amine and to isomerize any unreacted catalyst.

16. The method of claim 15, wherein the catalyst is S- or R-carvone, or a mixture thereof, and wherein the S- or R-carvone is isomerized to produce carvacrol, and further comprising recovering the carvacrol.

17. The method of claim 15, wherein the catalyst is dihydrocarvone and wherein the dihydrocarvone is isomerized to produce carvenone, and further comprising recovering the carvenone.

18. The method of claim 15, wherein the acid reaction mixture is heated to about 185° C. to about 190° C. for about 5 min., or more.

19. The method of claim 12, wherein the acid reaction mixture during step (e) is heated to about 50 to 80° C., or more, to hydrolyze the imine in equilibrium to form an amine, and further comprising:

(f) recovering the catalyst via extraction from the reaction mixture from step (e), and (g) performing an additional reflux on the acid reaction mixture at a temperature of about 120° C., or more, for about 5 min., or more, to isomerize any unreacted catalyst.

20. The method of claim 1, wherein the acid is a strong acid.

21. The method of claim 1, wherein the acid is any of HCl, $H_2SO_4$, $H_3PO_4$, and HBr.

22. The method of claim 1, further comprising:

(f) removing unreacted solvent and catalyst; and (g) recovering the amine.

23. The method of claim 22, wherein removing unreacted solvent and catalyst comprises washing the reaction mixture with ether and water solvent and distilling off the water, ether, solvent, and recovering an amine salt.

* * * * *